US012705655B2

(12) United States Patent
Shin et al.

(10) Patent No.: US 12,705,655 B2
(45) Date of Patent: Aug. 11, 2026

(54) SYSTEM FOR PROVIDING CUSTOMIZED COSMETICS

(71) Applicant: LG HOUSEHOLD & HEALTH CARE LTD., Seoul (KR)

(72) Inventors: Joong Gon Shin, Seoul (KR); Yun Kwan Kim, Seoul (KR); Bok Hyun Pack, Seoul (KR); Hae Young Hwang, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 227 days.

(21) Appl. No.: 17/790,447

(22) PCT Filed: Dec. 4, 2020

(86) PCT No.: PCT/KR2020/017630
§ 371 (c)(1),
(2) Date: Jun. 30, 2022

(87) PCT Pub. No.: WO2021/187722
PCT Pub. Date: Sep. 23, 2021

(65) Prior Publication Data

US 2023/0046151 A1 Feb. 16, 2023

(30) Foreign Application Priority Data

Mar. 17, 2020 (KR) ........................ 10-2020-0032647

(51) Int. Cl.
*G06Q 30/0601* (2023.01)
*A61B 5/00* (2006.01)
(Continued)

(52) U.S. Cl.
CPC ......... *G06Q 30/0621* (2013.01); *A61B 5/441* (2013.01); *B01F 33/8442* (2022.01);
(Continued)

(58) Field of Classification Search
CPC ........... G06Q 30/0621; G06Q 30/0631; G16H 50/20; B01F 33/8442; A61B 5/441; H04L 63/061; A45D 2044/007
See application file for complete search history.

(56) References Cited

U.S. PATENT DOCUMENTS 10,381,105 B1 * 8/2019 Tran ......................... G06N 5/04
2007/0118399 A1 5/2007 Avinash et al.
(Continued)

FOREIGN PATENT DOCUMENTS

CN 110036403 A 7/2019
JP 2018-73273 A 5/2018
(Continued)

OTHER PUBLICATIONS

KR20180078507A—translated (Year: 2018).*
(Continued)

*Primary Examiner* — Jason S Tiedeman
*Assistant Examiner* — Jonathan C Edouard
(74) *Attorney, Agent, or Firm* — Birch, Stewart, Kolasch & Birch, LLP

(57) ABSTRACT

The present disclosure relates to a system for providing customized cosmetics by using genetic information, the system comprising: a terminal that receives user information related to a user; a genetic/medical information server that stores genetic information related to the user; a skin meter that acquires skin information on the user; and a cosmetic manufacturing system that manufactures cosmetics by discharging at least one cosmetic material, wherein the cosmetic manufacturing system can select a cosmetic material to be discharged on the basis of at least one among the user information, the genetic information, and the skin information.

14 Claims, 15 Drawing Sheets

(51) Int. Cl.

| | |
|---|---|
| ***B01F 33/84*** | (2022.01) |
| ***G16H 50/20*** | (2018.01) |
| ***H04L 9/40*** | (2022.01) |
| *A45D 44/00* | (2006.01) |

(52) U.S. Cl.
CPC ......... *G06Q 30/0631* (2013.01); *G16H 50/20* (2018.01); *H04L 63/061* (2013.01); *A45D 2044/007* (2013.01)

(56) References Cited

U.S. PATENT DOCUMENTS

| | | | | |
|---|---|---|---|---|
| 2012/0041284 | A1 * | 2/2012 | Krishnan | A61B 5/448<br>600/306 |
| 2013/0066170 | A1 * | 3/2013 | Mattoli | A61B 5/6843<br>600/306 |
| 2015/0180879 | A1 * | 6/2015 | Hardt | H04L 63/105<br>726/4 |
| 2017/0360693 | A1 * | 12/2017 | Yakubov | A61P 17/00 |
| 2018/0260871 | A1 | 9/2018 | Harvill et al. | |
| 2019/0116180 | A1 * | 4/2019 | Teranishi | G06F 21/32 |
| 2019/0295728 | A1 * | 9/2019 | Jeong | A45D 44/00 |
| 2019/0347387 | A1 | 11/2019 | Woodward et al. | |

FOREIGN PATENT DOCUMENTS

| | | | | | |
|---|---|---|---|---|---|
| KR | 10-0874825 | B1 | | 12/2008 | |
| KR | 20110105571 | A | * | 9/2011 | |
| KR | 10-1555636 | B1 | | 9/2015 | |
| KR | 10-2017-0108363 | A | | 9/2017 | |
| KR | 10-2017-0117840 | A | | 10/2017 | |
| KR | 102049447 | B1 | * | 11/2017 | |
| KR | 20170130963 | A | * | 11/2017 | |
| KR | 10-2018-0078507 | A | | 7/2018 | |
| KR | 20180078507 | A | * | 7/2018 | |
| KR | 20180124482 | A | * | 11/2018 | |
| KR | 20180127941 | A | * | 11/2018 | |
| KR | 10-2019-0113005 | A | | 10/2019 | |
| KR | 20190122174 | A | * | 10/2019 | |
| KR | 10-2019-0129064 | A | | 11/2019 | |
| KR | 10-2020-0011728 | A | | 2/2020 | |
| KR | 102074178 | B1 | * | 2/2020 | |
| WO | WO 02/05061 | A2 | | 1/2002 | |
| WO | WO-2018044010 | A1 | * | 3/2018 | G06Q 30/0621 |
| WO | WO-2019191131 | A1 | * | 10/2019 | G16H 20/00 |
| WO | WO-2020016775 | A1 | * | 1/2020 | G06V 40/171 |

OTHER PUBLICATIONS

KR20110105571A—translated (Year: 2011).*
KR20180127941A—translated (Year: 2018).*
KR20180124482A—translated (Year: 2018).*
Fu, Yun, et al. "Age Synthesis and Estimation via Faces: A Survey." IEEE Transactions on Pattern Analysis and Machine Intelligence, vol. 32, No. 11, Nov. 2010, pp. 1955-1976. IEEE Xplore, https://doi.org/10.1109/TPAMI.2010.36. (Year: 2010).*
KR102049447B1—translated (Year: 2017).*
KR102074178B1—translated (Year: 2020).*
Liu, Xiaoran, et al. "A DNA-Based Intelligent Expert System for Personalised Skin-Health Recommendations." IEEE Journal of Biomedical and Health Informatics, vol. 24, No. 11, Nov. 2020, pp. 3276-3284. DOI.org (Crossref), https://doi.org/10.1109/JBHI.2020.2978667. (Year: 2020).*
KR20190122174A—translated (Year: 2019).*
KR20170130963A—translated (Year: 2017).*
WO-2018044010-A1_translated (Year: 2018).*
Zhang et al., "Research of Main Mode with a Pre-Shared Key in IKE Protocol," Journal of Nanjing University of Posts and Telecommunications (Natural Science), vol. 27, No. 5, Oct. 15, 2007, pp. 50-55, with English translation.

* cited by examiner

FIG. 12

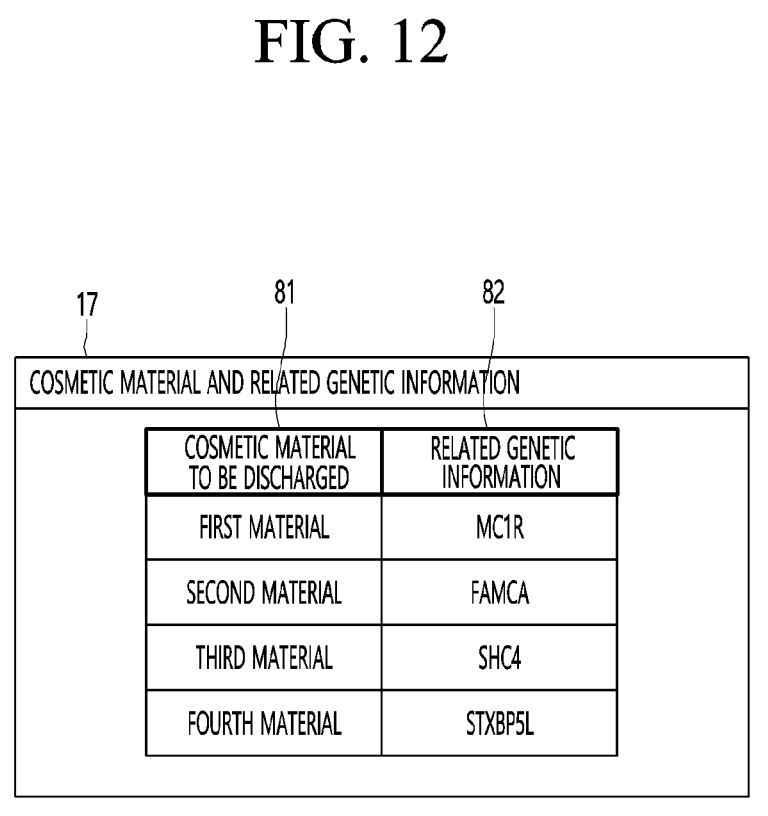

| COSMETIC MATERIAL TO BE DISCHARGED | RELATED GENETIC INFORMATION |
|---|---|
| FIRST MATERIAL | MC1R |
| SECOND MATERIAL | FAMCA |
| THIRD MATERIAL | SHC4 |
| FOURTH MATERIAL | STXBP5L |

COSMETIC MATERIAL AND RELATED GENETIC INFORMATION

| | COSMETIC MATERIAL TO BE DISCHARGED | RELATED GENETIC INFORMATION | PRICE |
|---|---|---|---|
| CHANGE | FIRST MATERIAL | WRINKLES | A WON |
| CHANGE | SECOND MATERIAL | PIGMENTATION | B WON |
| CHANGE | THIRD MATERIAL | WHITENING | C WON |
| CHANGE | FOURTH MATERIAL | WRINKLES | D WON |

84

SYSTEM FOR PROVIDING CUSTOMIZED COSMETICS

CROSS REFERENCE TO RELATED APPLICATIONS

This application is the National Phase of PCT International Application No. PCT/KR2020/017630, filed on Dec. 4, 2020, which claims priority under 35 U.S.C. 119(a) to Patent Application No. 10-2020-0032647, filed in the Republic of Korea on Mar. 17, 2020, all of which are hereby expressly incorporated by reference into the present application.

TECHNICAL FIELD

The present disclosure relates to a system for providing customized cosmetics.

BACKGROUND ART

Recently, the kinds of cosmetics have become very diverse according to the development of beauty industry. Specifically, there are cosmetics for dry skin, neutral skin and oily skin, and the like according to a skin type, cosmetics such as beige and pink beige according to a skin color, and various cosmetics for whitening, for improving wrinkles, for blocking ultraviolet rays, and the like according to functions.

However, despite the variety of cosmetics, since each user has different skin characteristics, hair characteristics, and the like, there is a limit to manufacture in advance and supply cosmetics suitable for each user. Accordingly, a cosmetic manufacturing device for providing a user with the cosmetics suitable for each user has been developed.

The cosmetic manufacturing device may manufacture cosmetics customized according to preference and taste for each user to provide the cosmetics to the user.

Meanwhile, the user may easily recognize his or her skin characteristics, but it is difficult to predict whether there will be more pigmentation or wrinkles in the future. Therefore, there is a limitation that it is difficult for the user to know which cosmetic material, particularly, which functional cosmetic material should be included in the cosmetics when manufacturing the customized cosmetic.

DISCLOSURE

Technical Problem

The present disclosure is directed to manufacturing customized cosmetics by predicting skin characteristics of a user.

The present disclosure is directed to manufacturing the customized cosmetics using the skin characteristics of the user predicted through genetic information.

The present disclosure is directed to enhancing the security of each user's genetic information used in the manufacture of customized cosmetics.

The present disclosure is directed to manufacturing cosmetics using not only the genetic information but also current skin condition, survey information, and the like.

The present disclosure is directed to providing the user with a predicted aging image through the genetic information.

The present disclosure is directed to providing various information on a cosmetic material to be discharged.

Technical Solution

A system for providing customized cosmetics according to an embodiment of the present disclosure includes a terminal that receives user information related to a user, a gene/medical information server that stores genetic information related to the user, a skin meter that acquires skin information on the user, and a cosmetic manufacturing system that manufactures cosmetics by discharging at least one cosmetic material, wherein the cosmetic manufacturing system may select the cosmetic material to be discharged on the basis of at least one of the user information, the genetic information, and the skin information.

The terminal may include a user identification unit for identifying the user, and the system for providing customized cosmetics using the genetic information may further include a key authentication server that shares a public key when a user is identified through the user identification unit, and a genetic/medical information server that transmits the genetic information to the cosmetic manufacturing system when receiving a server key generated based on the public key.

The cosmetic manufacturing system may determine a skin of the user as any one of preset skin groups based on the genetic information, and may select the cosmetic material to be discharged based on the determined skin group.

The cosmetic manufacturing system may determine a skin of the user as any one of preset skin groups in consideration of a preset priority among the user information, the genetic information, and may select the cosmetic material to be discharged based on the determined skin group.

The cosmetic manufacturing system may determine a group to which the skin of the user belongs based on the skin information, and may determine a subgroup to which the skin of the user belongs within the determined group using the genetic information to select the cosmetic material to be discharged.

The terminal may receive survey information as the user information, and the cosmetic manufacturing system may correct a compounding ratio of the cosmetic material to be discharged that is selected based on the survey information.

The terminal may display a predicted aging image derived based on the genetic information.

The terminal may display genetic information related to the selected cosmetic material.

The terminal may display at least one of the selected cosmetic material, variable information of the selected cosmetic material, and price information of the cosmetic material, and may further receive an input for changing the cosmetic material.

The cosmetic manufacturing system may select the cosmetic material to be discharged using data in which a related gene for predicting skin characteristics and a skin group classified according to skin characteristics are mapped.

The cosmetic manufacturing system may select the cosmetic material to be discharged using data in which the skin group classified according to the skin characteristics and cosmetic materials suitable for each skin group are mapped.

Advantageous Effects

According to the present disclosure, since customized cosmetics are manufactured by predicting skin characteristics of a user, there is an advantage that pigmentation, wrinkles, and the like can be prevented in advance.

According to the present disclosure, since the customized cosmetics are manufactured by predicting the skin characteristics of the user through genetic information, there is an advantage that cosmetics in consideration of skin characteristics that are difficult for the user to know can be provided to the user.

According to the present disclosure, when genetic/medical information are used for manufacturing the cosmetics, there is an advantage that the genetic/medical information are safely protected.

According to the present disclosure, since the cosmetics are manufactured based on not only the genetic/medical information but also a current skin condition, survey information, and the like, there is an advantage that customized cosmetics in consideration of both a future skin condition and the current skin condition of the user are provided.

According to the present disclosure, there is an advantage of assisting the user in selecting cosmetics through information such as a predicted aging image, a cosmetic material to be discharged, and the like.

DESCRIPTION OF DRAWINGS

FIG. 12 is an exemplary view of a method for the terminal according to the embodiment of the present disclosure to display a selected cosmetic material and genetic information related to the selected cosmetic material.

FIG. 13 is an exemplary view a method for the terminal according to the embodiment of the present disclosure to display a selected cosmetic material, variable information of the selected cosmetic material, and price information of the cosmetic material.

MODES OF THE PRESENT INVENTION

Figure 1:
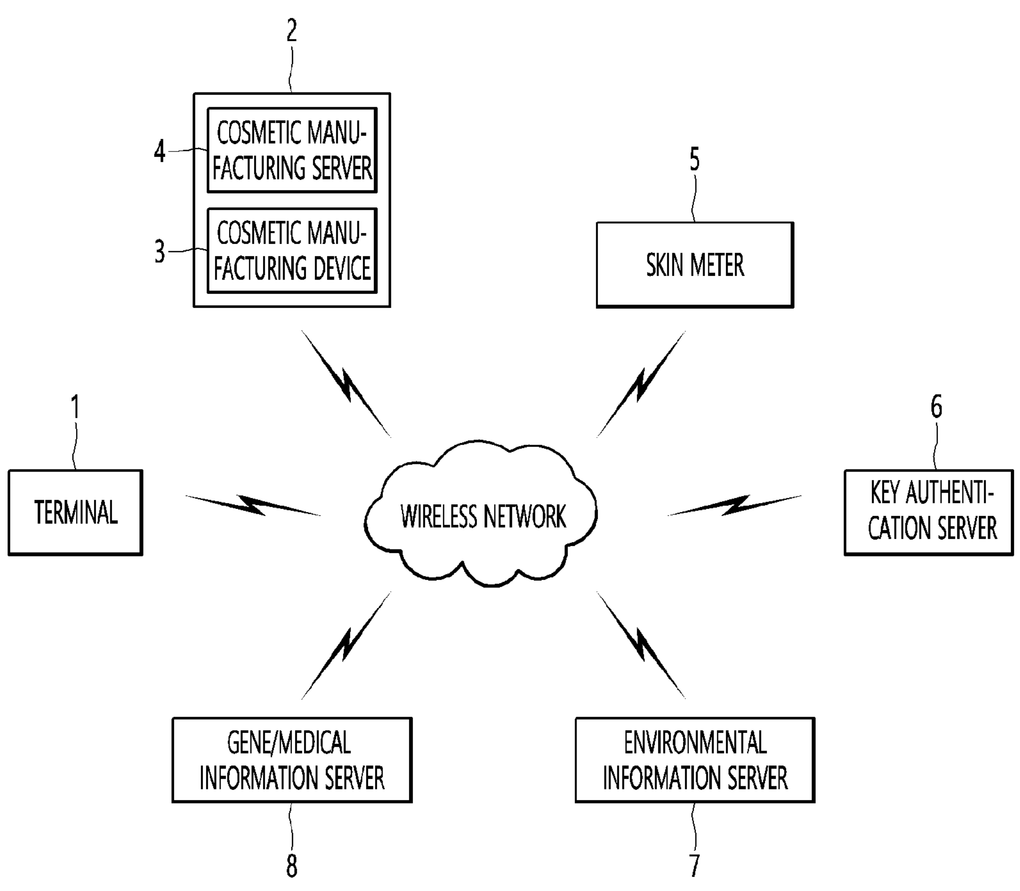
FIG. 1 is a control block diagram of a system for providing customized cosmetics using genetic information according to an embodiment of the present disclosure.

Hereinafter, embodiments will be described in detail with reference to the accompanying drawings, however, the same components are designated by the same reference numerals, and repeated description thereof will be omitted.

Suffixes "module" and "part" for elements used in the following descriptions are given or used just for convenience in writing the specification, and do not have meanings or roles distinguishable between them.

In addition, in describing embodiments of the present disclosure, when detailed description of a known function is deemed to unnecessarily blur the gist of the present disclosure, the detailed description will be omitted. Further, accompanying drawings are only for easily understanding embodiments disclosed in the present disclosure, and the technical spirit disclosed in the present disclosure are not limited by the accompanying drawings, and it should be understood that the present invention includes all modifications, equivalents, and alternatives falling within the spirit and scope of the claims.

It should be understood that, although the terms first, second, and the like may be used herein to describe various elements, these elements are not limited by these terms. The terms are only used to distinguish one element from another.

Elements referred to in singular may be number one or more, unless the context clearly indicates otherwise.

It should be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

FIG. 1 is a control block diagram of a system for providing customized cosmetics using genetic information according to an embodiment of the present disclosure.

The system for providing customized cosmetics using the genetic information may include at least some or all of a terminal 1, a cosmetic manufacturing system 2, a skin meter 5, a key authentication server 6, an environmental information server 7, and a gene/medical information server 8

The terminal 1, the cosmetic manufacturing system 2, the skin meter 5, the key authentication server 6, the environmental information server 7, and the gene/medical information server 8 may each communicate with each other through a wireless network.

In addition, the cosmetic manufacturing system 2 may include at least one of a cosmetic manufacturing device 3 and a cosmetic manufacturing server 4. The cosmetic manufacturing device 3 and the cosmetic manufacturing server 4 may transmit and receive signals by wire or wirelessly.

The terminal 1 may receive various information related to cosmetic manufacturing. In the present specification, cosmetics may include not only beauty products used for a skin of a user such as foundation, sun cream, basic cosmetics, color cosmetics, etc., but also beauty products used for a hair of the user such as a hair dye, and products used for nails or toenails of the user such as manicure, gel manicure, etc.

In addition, the terminal 1 may receive an input for controlling an operation of the cosmetic manufacturing device 3 from the user, and in this case, the terminal 1 may transmit a signal for controlling the cosmetic manufacturing device 3 to operate according to the input information to the cosmetic manufacturing device 3.

For example, the terminal 1 may receive information related to cosmetics manufacturing, and when the input information related to the cosmetics manufacturing is transmitted to the cosmetic manufacturing device 3, the cosmetic manufacturing device 3 may calculate the method of manufacturing the cosmetics. The cosmetic manufacturing device 3 may calculate the method of manufacturing the cosmetics based on information stored in an internal memory or may calculate the method of manufacturing the cosmetics through the cosmetic manufacturing server 4.

The terminal 1 may receive user information. The terminal 1 may receive the user information related to the user.

The terminal 1 may display various screens for receiving information related to cosmetics manufacturing.

In addition, the terminal 1 may display operation information on the cosmetic manufacturing device 3. For example, the terminal 1 may display a current state of the cosmetic manufacturing device 3, information on cosmetics to be provided from the cosmetic manufacturing device 3, a simulation, and the like.

The terminal 1 may be a smart phone, but this is merely illustrative, and may include a wearable device such as a smart watch, a tablet PC, a laptop computer, a desktop, and the like.

The terminal 1 may store a public key and a private key described later, separately.

The cosmetic manufacturing device 3 may be a device for providing cosmetics.

The cosmetic manufacturing device 3 may provide the cosmetics according to a signal received from the terminal 1. According to an embodiment, the cosmetic manufacturing device 3 may provide a plurality of cosmetic materials and manufacture the cosmetics by discharging and/or mixing the provided cosmetic materials to provide the cosmetics. According to another embodiment, the cosmetic manufacturing device 3 may provide cosmetics and discharge the cosmetics that have already been manufactured to be used immediately to provide the cosmetics.

Hereinafter, it is assumed that the cosmetic manufacturing device 3 provides cosmetics manufactured by discharging and/or mixing a plurality of cosmetic materials, but this is merely illustrative for convenience of description, and thus it is reasonable that the present disclosure is not limited thereto.

The cosmetic manufacturing device 3 may communicate with the cosmetic manufacturing server 4. The cosmetic manufacturing server 4 may store various information related to cosmetic manufacturing. For example, the cosmetic manufacturing server 4 may store data required for calculation of the method of manufacturing the cosmetics, information on pre-manufactured cosmetics, user information, and the like.

The skin meter 5 may acquire skin information on the user. The skin information may refer to information on a skin condition such as dryness of the skin, moisture content, pigmentation, wrinkles, skin color, and the like. The skin meter 5 may measure the skin condition of the user.

The skin meter 5 may be separately provided as shown in FIG. 1, or may be provided as a configuration of the terminal 1 and the like to measure the skin condition.

The user terminal 1, the cosmetic manufacturing device 3, and the skin meter 5 may be separately provided, respectively, or provided in one device, and when their functions may be performed, it is not limited to whether the device is separated or not.

The key authentication server 6 is a server for protecting information used in the manufacture of cosmetics, in particular, user information. For example, the key authentication server 6 may be a server that exchanges the public key and the private key for protecting genetic information/medical information and the like.

The key authentication server 6 may authenticate the public key of the user, and may manage the public key, a master key, and the like of the gene/medical information server 8.

The environmental information server 7 may be a server that provides environmental information used for cosmetics manufacturing to the terminal 1 or the cosmetic manufacturing system 2. The environmental information may include weather information such as temperature, humidity, amount of fine dust, season, fashion information such as popular cosmetic materials. and the like.

The genetic/medical information server 8 may store at least one of genetic information and medical information of each user. That is, the gene/medical information server 8 may store genetic/medical information related to the user.

The genetic information may be information on a preset number of genes selected to be relevant to skin characteristics. The genetic information may be information on a gene selected based on literature research for an individual gene SNP screening study. For example, the gene/medical information server 8 may include information in which users with high pigmentation or dark skin color may be distinguished through information screening in BNC2, MC1R, PPARGC1B, MFSD12, and FANCA genes, and users with many wrinkles may be distinguished through information screening in HR, COL1A2, MMP1, SHC4, and STXBP5L genes.

The medical information may be information on a medical record of an individual user.

Figure 2:
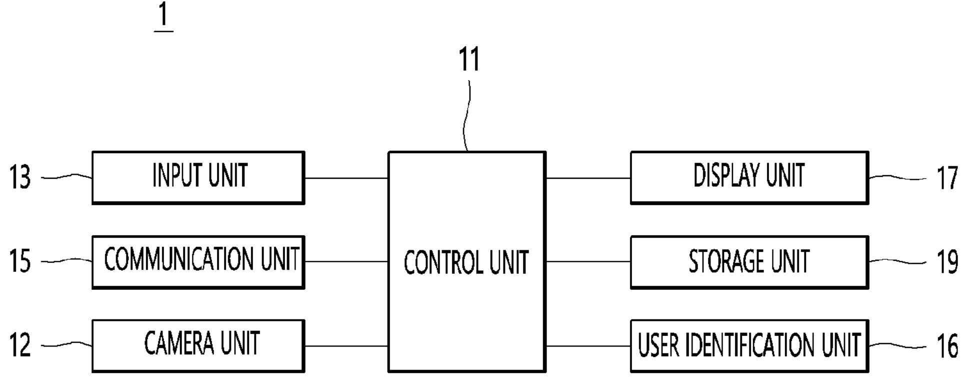
FIG. 2 is a control block diagram of a terminal according to an embodiment of the present disclosure.

FIG. 2 is a control block diagram of a terminal according to an embodiment of the present disclosure.

The terminal 1 may include at least some or all of a control unit 11, an input unit 13, a communication unit 15, a camera unit 12, a display unit 17, a storage unit 19, and a user identification unit 16.

The control unit 11 may control an overall operation of the terminal 1. The control unit 11 may control each of the input unit 13, the communication unit 15, the camera unit 12, the display unit 17, the storage unit 19, and the user identification unit 16.

The input unit 13 may receive various information from the user. For example, the input unit 13 may receive information related to manufacturing cosmetics, user information, and the like.

The user information may include at least one of personal information, schedule information, and survey information.

The personal information may include information on age, gender, race, and the like.

The schedule information may include information on a date, time, place, etc. for each of the scheduled schedules.

The survey information may include information on answers to questions related to skin diagnosis, cosmetics manufacturing, and the like.

The input unit 13 may be formed of a touch screen or the like, or may include a physical key button.

The communication unit 15 may communicate with the cosmetic manufacturing system 2. For example, the communication unit 15 may transmit the user information to the cosmetic manufacturing system 2.

The communication unit 15 may include a short-range communication module (not shown), such as a mobile communication module (not shown), a Bluetooth module (not shown), and the like, in order to communicate with the cosmetic manufacturing system 2 and the like.

The camera unit 12 may capture a user.

The display unit 17 may display a screen for receiving various information from the user. As an example, the display unit 17 may display a screen for receiving the user information. As another example, the display unit 17 may display a simulation.

As described above, the display unit 17 may display information related to an operation of the terminal 1 and information related to the operation of the cosmetic manufacturing device 3.

The storage unit 19 may store various information related to the operation of the terminal 1.

The user identification unit 16 may identify a user. The user identification unit 16 may include a module for identifying the user, for example, it may include at least one of a fingerprint recognition unit (not shown), a microphone (not shown), an IR sensor (not shown), and the like. The fingerprint recognition unit (not shown) may identify the user by analyzing the fingerprint. The microphone (not shown) may identify the user by analyzing a voice of the user. The IR sensor (not shown) may identify the user by analyzing a pulse of the user.

In addition, the camera unit 12 may be a configuration of the user identification unit 16, and in this case, the camera unit 12 may identify the user by analyzing an iris, a face, or the like. When the camera unit 12 analyzes the iris, the accuracy of user identification through the iris may be improved by using the reflectivity recognized through the IR sensor (not shown).

The user identification unit 16 may identify the user using complex biometric information acquired by using a plurality of a fingerprint recognition unit (not shown), a microphone (not shown), an IR sensor (not shown), and the camera unit 12.

Meanwhile, components of the terminal 1 shown in FIG. 2 are merely illustrative, some of the components shown in FIG. 2 may be omitted, or additional components may be further added in addition to the components shown in FIG. 2.

Figure 3:
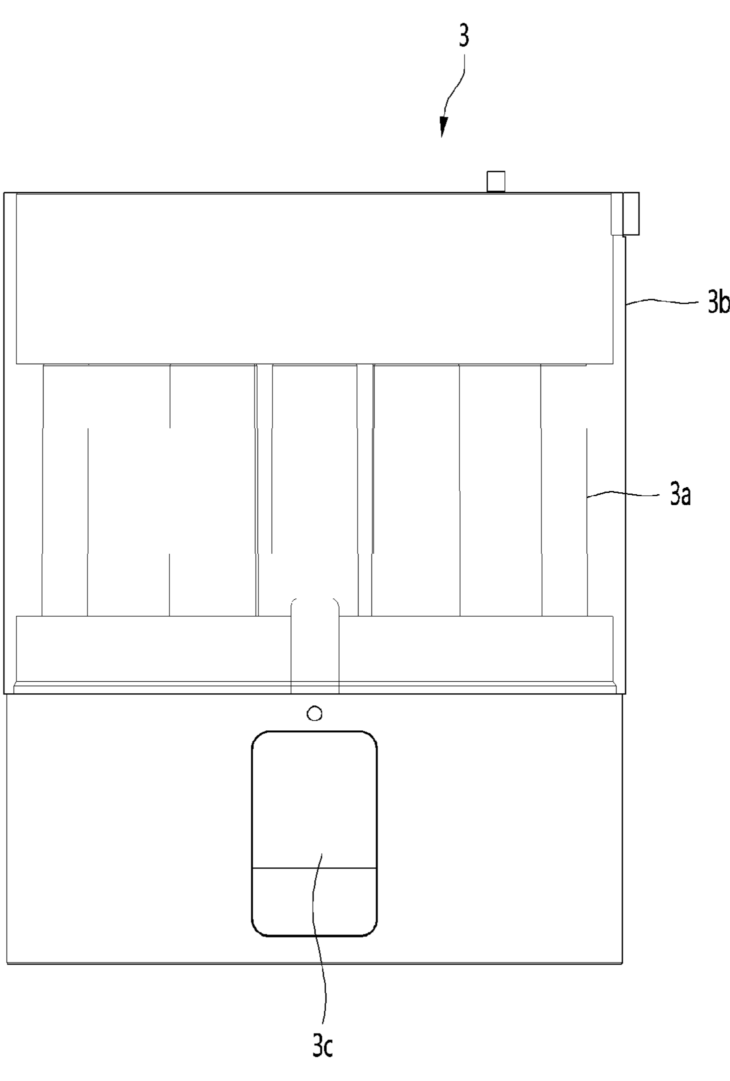
FIG. 3 is an exemplary view illustrating a cosmetic manufacturing device according to an embodiment of the present disclosure.

FIG. 3 is an exemplary view illustrating a cosmetic manufacturing device according to an embodiment of the present disclosure.

The cosmetic manufacturing device 3 may manufacture cosmetics by discharging at least one cosmetic material.

The cosmetic manufacturing device 3 may include a plurality of cartridges 3*a* that includes a cosmetic material and a case 3*b* that accommodates the cartridges 3*a*. The cosmetic material used for manufacturing cosmetics may be provided in each of the plurality of cartridges 3*a*. In addition, a door 3*c* through which cosmetics are provided may be formed in the case 3*b*. The cosmetics manufactured in the cosmetic manufacturing device 3 may be provided to the user through the door 3*c*.

Meanwhile, the cosmetic manufacturing device 3 shown in FIG. 3 is merely illustrative, and the cosmetic manufacturing device 3 may include all devices capable of providing cosmetics.

The cosmetic material may include raw materials, synthetic materials, etc. used in the manufacture of cosmetics.

The cosmetic manufacturing device 3 may manufacture cosmetics by discharging the cosmetic material from at least one of the plurality of cartridges 3*a* according to the method of manufacturing the cosmetics.

Figure 4:
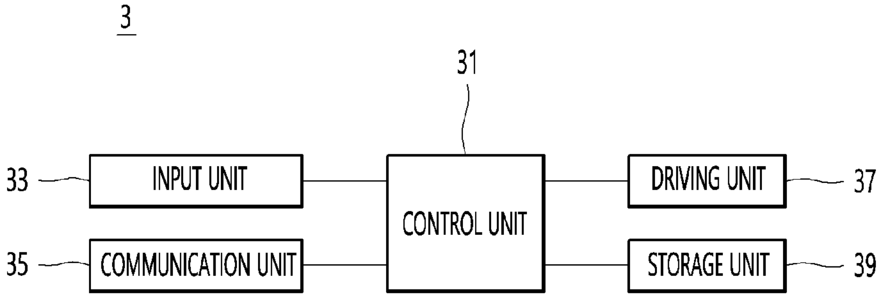
FIG. 4 is a control block diagram of a cosmetic manufacturing device according to an embodiment of the present disclosure.

FIG. 4 is a control block diagram of a cosmetic manufacturing device according to an embodiment of the present disclosure.

The cosmetic manufacturing device 3 may include at least one of a control unit 31, an input unit 33, a communication unit 35, a driving unit 37, and a storage unit 39.

The controller 31 may control the overall operation of the cosmetic manufacturing device 3. The control unit 31 may control each of the input unit 33, the communication unit 35, the driving unit 37, and the storage unit 39.

The input unit 33 may receive various information from the user. For example, the input unit 33 may receive information related to manufacturing cosmetics, and in this case, the cosmetic manufacturing device 3 may manufacture cosmetics without receiving information related to manufacturing cosmetics from the terminal 1. That is, according to the embodiment, the cosmetic manufacturing device 3 may directly receive the information related to manufacturing cosmetics to calculate the method of manufacturing the cosmetics.

In addition, the input unit 33 may receive a cosmetic manufacturing command, a cosmetic manufacturing stop command, and the like.

The input unit 33 may be formed of a touch screen or the like, or may include a physical key button.

The communication unit 35 may communicate with an external device such as the terminal 1. The communication unit 35 may include a short-range communication module (not shown) such as a mobile communication module (not shown) and a Bluetooth module (not shown), and the like.

The communication unit 35 may communicate with the cosmetic manufacturing server 4.

The driving unit 37 may operate to manufacture cosmetics according to the method of manufacturing the cosmetics. The driving unit 37 may be driven to discharge the cosmetic material accommodated in the at least one cartridge 3*a* so that the cosmetics are manufactured. For example, the driving unit 37 may include a cartridge rotation motor (not shown), a discharge motor (not shown), a container transfer motor (not shown), and the like that operate to discharge the cosmetic material from the at least one cartridge 3*a*, but this is merely illustrative for convenience of description.

The storage unit 39 may store cosmetic manufacturing information. The cosmetic manufacturing information may include a method of driving cosmetics to be manufactured according to the method of manufacturing the cosmetics.

In addition, the storage unit 39 may store data necessary for calculation of the method of manufacturing the cosmetics. Alternatively, the cosmetic manufacturing server 4 stores the data necessary for the calculation of the method of manufacturing the cosmetics, so that the cosmetic manufacturing server 4 may calculate the method of manufacturing the cosmetics, and the cosmetic manufacturing device 3 may receive the method of manufacturing the cosmetics from the cosmetic manufacturing server 4.

Meanwhile, components of the cosmetic manufacturing device 3 shown in FIG. 4 are merely illustrative, some of the components shown in FIG. 4 may be omitted, or additional components may be further added in addition to the components shown in FIG. 4. For example, the cosmetic manufacturing device 3 may further include a display unit (not shown) for displaying operation information and the like of the cosmetic manufacturing device 3.

Next, a method of operating a system for providing customized cosmetics using genetic information according to an embodiment of the present disclosure will be described.

Figure 5:
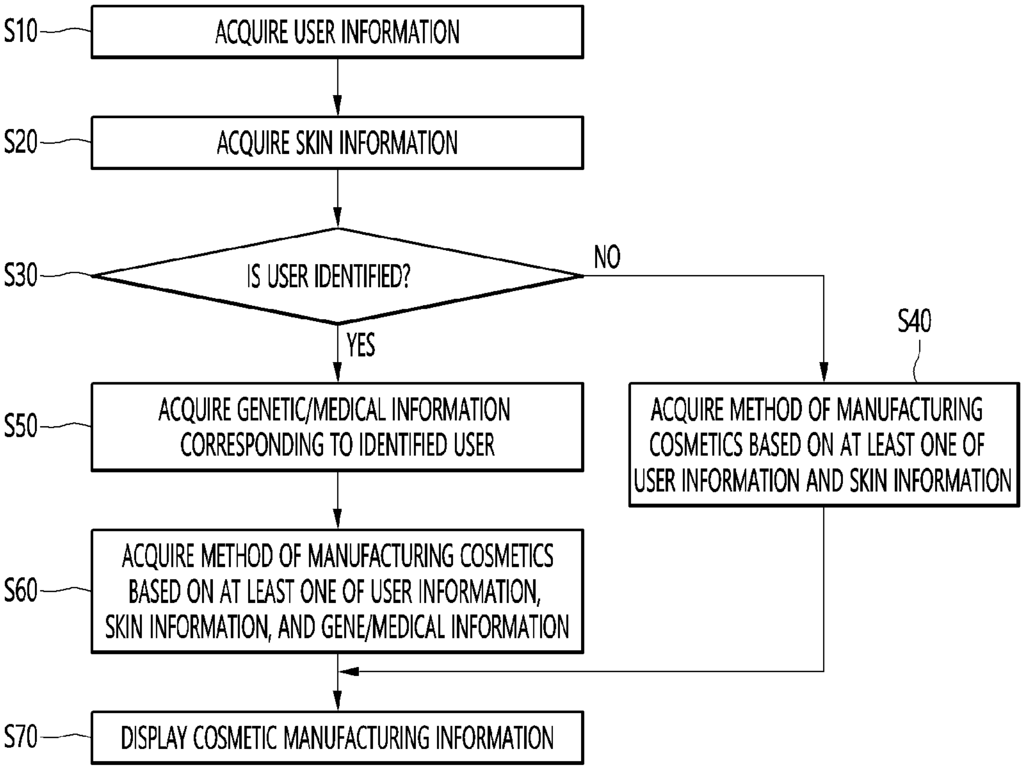
FIG. 5 is a flowchart illustrating a method of operating a terminal according to an embodiment of the present disclosure.

FIG. 5 is a flowchart illustrating a method of operating a terminal according to an embodiment of the present disclosure.

The control unit 11 may acquire user information (S10).

The control unit 11 may acquire user information input through the input unit 13.

Figure 6:
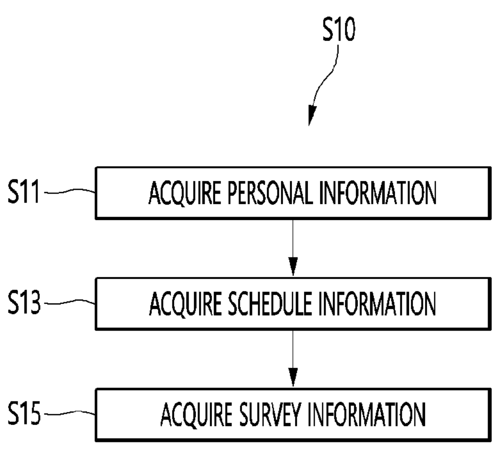
FIG. 6 is a flowchart illustrating a method for a terminal to acquire user information according to an embodiment of the present disclosure.

FIG. 6 is a flowchart illustrating a method for a terminal to acquire user information according to an embodiment of the present disclosure.

FIG. 6 may be a flowchart in which step S10 of FIG. 5 is embodied.

The control unit 11 may acquire personal information (S11).

For example, the control unit 11 may acquire the age, gender, race, etc. of the user who will use the cosmetics.

The control unit 11 may acquire schedule information (S13).

For example, the control unit 11 may acquire information on the date, time, place, etc. for each schedule scheduled from the user who will use the cosmetics.

The control unit 11 may acquire survey information (S15).

Specifically, when the display unit 17 displays at least one question, the input unit 13 may receive an answer to the displayed question, and the control unit 11 may acquire the survey information including the question and the answer.

For example, the question may be about lifestyle and the like. An example of a question about the lifestyle may be a question about whether the user spends a lot of time outdoors or eats meat often.

Meanwhile, in FIG. 6, it is illustrated that the control unit 11 acquires all of personal information, schedule information, and survey information as user information, but the control unit 11 may acquire some of the personal information, the schedule information, and the survey information as the user information.

FIG. 5 will be described again.

The control unit 11 may acquire skin information (S20).

The skin information is information on the skin condition, and may include information on the dryness of the skin, the amount of moisture, whether pigmentation is present, the degree of wrinkles, the color of the skin, and the like.

As an example, the control unit 11 may acquire the skin information by analyzing the skin of the user captured through the camera unit 12. As another example, the control unit 11 may acquire the skin information by receiving the skin information from the skin meter 5 through the communication unit 15. However, the above-described embodiments are merely illustrative, and the control unit 11 may acquire the skin information in various ways.

The control unit 11 may determine whether the user may be identified (S30).

The control unit 11 may identify the user through the user identification unit 16.

When the control unit 11 may not identify the user, it may acquire the method of manufacturing the cosmetics based on at least one of the user information and the skin information (S40). The user information and the skin information may be information input by the user or information measured by the skin meter.

Step S40 is the same as step S60 except that the type of information used to acquire the method of manufacturing the cosmetics is different, and thus it will be described in detail in step S60.

When the control unit 11 can identify the user, it may identify the user and acquire genetic/medical information corresponding to the identified user (S50).

According to an embodiment, the control unit 11 may acquire all of the genetic/medical information corresponding to the identified user.

According to another embodiment, the control unit 11 may acquire a security level when identifying the user, and may differently determine the type and amount of genetic/medical information to be acquired according to the security level.

Next, a method of differently acquiring genetic/medical information according to a security level according to an embodiment of the present disclosure will be described with reference to FIG. 7.

Figure 7:
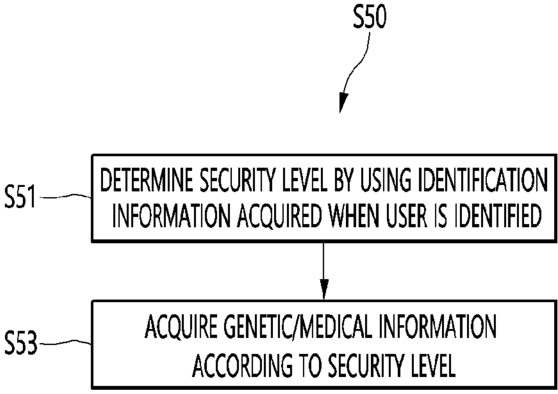
FIG. 7 is a flowchart illustrating a method of acquiring genetic/medical information according to an embodiment of the present disclosure.

FIG. 7 is a flowchart illustrating a method of acquiring genetic/medical information according to an embodiment of the present disclosure.

FIG. 7 may be a flowchart in which step S50 of FIG. 5 is embodied.

The control unit 11 may determine the security level by using the identification information acquired when the user is identified (S51).

The identification information is information acquired through the user identification unit 16, and may include biometric information such as face information, iris information, fingerprint information, pulse information, and voice information. In addition, the identification information may include an ID and a password.

According to an embodiment, the control unit 11 may determine the security level based on the type of identification information acquired when identifying the user.

For example, the control unit 11 may determine the security level as a first level when the ID and password are acquired as identification information, may determine the security level as a second level when the face information is acquired as the identification information, and may determine the security level as a third level when the iris information is acquired as the identification information.

According to another embodiment, the control unit 11 may determine the security level based on the number of identification information acquired when identifying the user.

Figure 8:
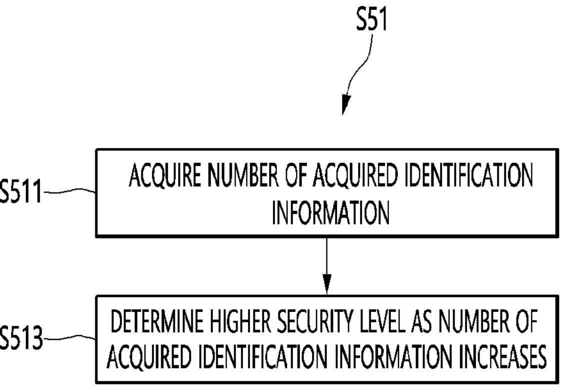
FIG. 8 is a flowchart illustrating a method of determining a security level to acquire genetic/medical information according to an embodiment of the present disclosure.

FIG. 8 is a flowchart illustrating a method of determining a security level to acquire genetic/medical information according to an embodiment of the present disclosure.

FIG. 8 may be a flowchart in which step S51 of FIG. 7 is embodied.

The control unit 11 may acquire the number of acquired identification information (S511).

The control unit 11 may determine a higher security level as the number of acquired identification information increases (S513).

Specifically, the control unit 11 may acquire the security level as the first level when the identification information identified as the user is acquired less than a first piece, the control unit 11 may acquire the security level as the second level when the identification information identified as the user is acquired the first piece or more and less than a second piece, and the control unit 11 may acquire the security level as a third level when the identification information identified as the user is acquired the second piece or more. That is, the control unit 11 may acquire the security level based on the number of identification information identified as the user.

FIG. 7 will be described again.

The control unit 11 may acquire the genetic/medical information according to the security level (S53).

The control unit 11 may acquire the genetic/medical information by varying the type and amount according to the security level.

For example, when the security level is the first level, the control unit 11 may acquire only the genetic information, when the security level is the second level, the control unit 11 may acquire only the medical information, and when the security level is the third level, the control unit 11 may acquire both the genetic information and the medical information.

As another example, when the security level is the first level, the control unit 11 may acquire only 30% of the genetic information on the user, when the security level is the second level, the control unit 11 may acquire only 60% of the genetic information on the user, and when the security level is the third level, the control unit 11 may acquire 100% of the genetic information on the user.

As described above, the control unit 11 may acquire the genetic/medical information corresponding to the identified user in various ways.

Meanwhile, the terminal 1 may directly acquire the genetic/medical information, but the cosmetic manufacturing system 2 may also acquire the genetic/medical information. That is, in step S50, the gene/medical information corresponding to the identified user may be transmitted from the gene/medical information server 8 to the terminal 1, but it is possible to acquire the genetic/medical information by transmitting the information from the gene/medical information server 8 to the cosmetic manufacturing system 2.

When the genetic/medical information is directly transmitted to the cosmetic manufacturing system 2, the security of the genetic/medical information may be further strengthened. In particular, the terminal 1 controls so that the genetic/medical information is transmitted to the cosmetic manufacturing system 5 through key authentication with the key authentication server 6, thereby minimizing a problem of exposing the genetic/medical information to the outside.

Figure 9:
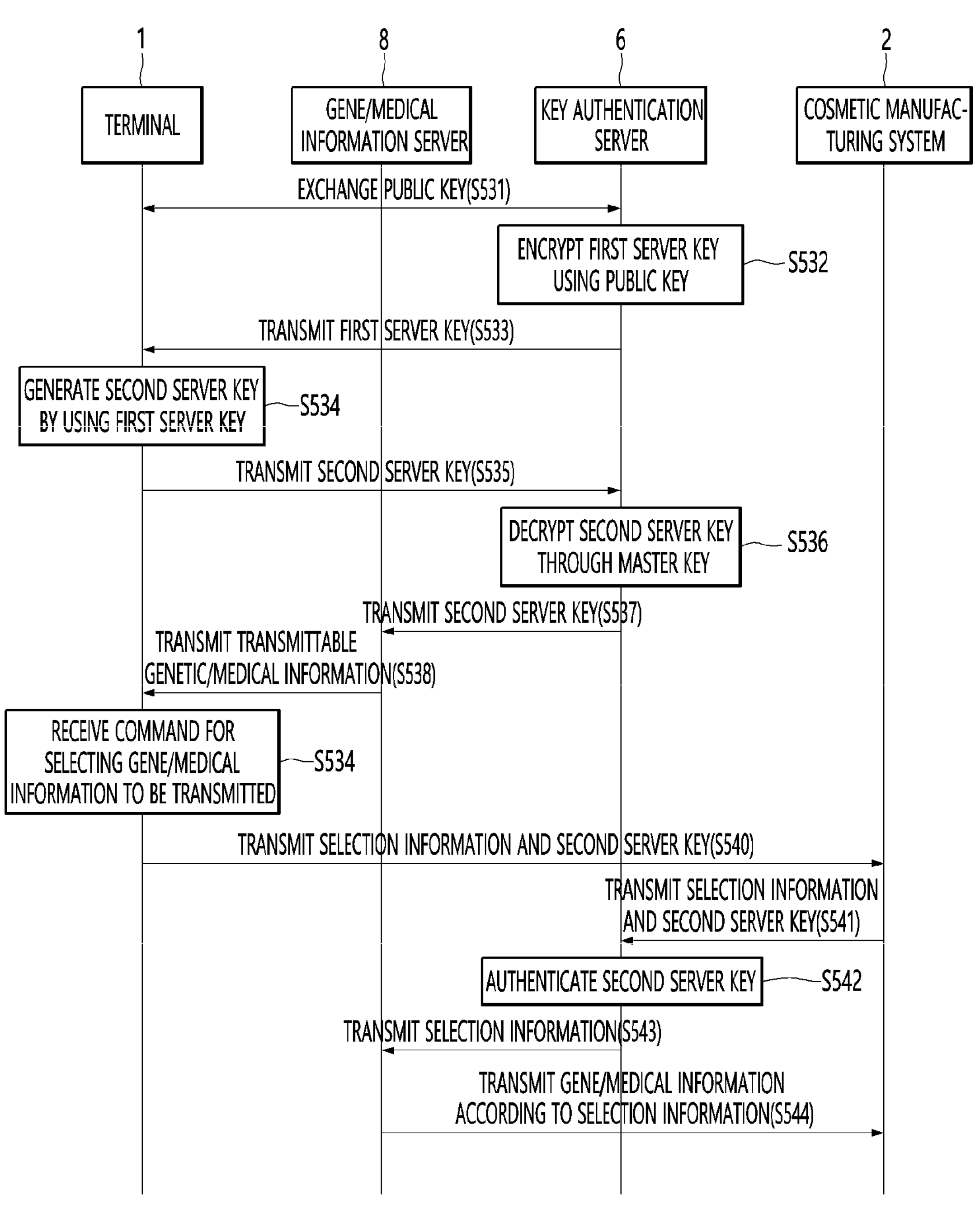
FIG. 9 is a flowchart illustrating a method of acquiring genetic/medical information in a system for providing customized cosmetics using genetic information according to an embodiment of the present disclosure.

FIG. 9 is a flowchart illustrating a method of acquiring genetic/medical information in a system for providing customized cosmetics using genetic information according to an embodiment of the present disclosure.

The terminal 1 may exchange a public key with the key authentication server 6 (S531).

That is, the terminal 1 may exchange the public key with the key authentication server 6 by transmitting the public key to the key authentication server 6. In particular, the terminal 1 may share the public key with the key authentication server 6 when the user is identified through the user identification unit 16.

Such a public key is valid only for a certain period of time, and may be regenerated after a certain period of time has elapsed. When the public key is regenerated, the steps to be described below may be performed again.

The key authentication server 6 may encrypt a first server key using the public key (S532).

For example, the key authentication server 6 may encrypt the first server key by applying the SHA-256/AES128 hash function.

The key authentication server 6 may transmit the encrypted first server key to the terminal 1 (S533).

The terminal 1 may receive the first server key from the key authentication server 6.

The terminal 1 may generate a second server key by using the first server key (S534).

The terminal 1 may generate the second server key by using the first server key through a preset algorithm with the key authentication server 6. Accordingly, as will be described later, the key authentication server 6 may decrypt the second server key, and servers other than the key authentication server 6 may not decrypt the second server key.

The terminal 1 may transmit the generated second server key to the key authentication server 6 (S535).

The key authentication server 6 may receive the second server key from the terminal 1.

The key authentication server 6 may decrypt the second server key through the master key (S536).

The key authentication server 6 may confirm the second server key through decryption and transmit the confirmed second server key to the gene/medical information server 8 (S537).

When the gene/medical information server 8 receives the server key (second server key) generated based on the public key, it may transmit the gene/medical information to the cosmetic manufacturing system 2. According to an embodiment, the gene/medical information server 8 may transmit all of the gene/medical information corresponding to the user to the cosmetic manufacturing system 2. According to another embodiment, the gene/medical information server 8 may transmit only a part selected by the user from the gene/medical information corresponding to the user to the cosmetic manufacturing system 2. Steps S538 to S544 of FIG. 9 may be specific steps in which only some genetic/medical information selected by the user is provided to the cosmetic manufacturing system 2.

When receiving the second server key from the key authentication server 6, the gene/medical information server 8 may transmit transmittable genetic/medical information (S538).

In this case, the transmittable genetic/medical information may be genetic/medical information acquired according to the security level described in FIG. 7.

When receiving the transmittable gene/medical information from the gene/medical information server 8, the terminal 1 may receive a command for selecting the gene/medical information to be transmitted (S534).

That is, the terminal 1 may receive a command for selecting the gene/medical information to be transmitted to the actual cosmetic manufacturing system 2 from among the genetic/medical information that can be transmitted. As a specific example, the terminal 1 may control the display unit 17 to display the transmittable genetic/medical information and receive a command to select at least one of the displayed transmittable genetic/medical information through the input unit 13.

The terminal 1 may transmit selection information and the second server key to the cosmetic manufacturing system 2 (S540).

Here, the selection information may indicate the gene/medical information to be transmitted that is selected through step S534.

When receiving the selection information and the second server key from the terminal 1, the cosmetic manufacturing system 2 may transmit the selection information and the second server key to the key authentication server 6 (S541).

When the key authentication server 6 receives the selection information and the second server key from the cosmetic manufacturing system 2, it may authenticate the second server key (S542).

When the second server key is authenticated, the key authentication server 6 may transmit the selection information to the gene/medical information server 8 (S543).

When the gene/medical information server 8 receives the selection information, it may transmit the gene/medical information according to the selection information to the cosmetic manufacturing system 2 (S544).

According to the embodiment, the genetic/medical information server 8 may transmit the genetic/medical information to the terminal 1.

That is, the gene/medical information server 8 may transmit the gene/medical information to be transmitted that is selected through the terminal 1 to the cosmetic manufacturing system 2.

In this way, the genetic/medical information of each user stored in the gene/medical information server 8 may be safely provided to the cosmetic manufacturing system 2.

FIG. 5 will be described again.

When acquiring the gene/medical information, the control unit 11 may acquire the method of manufacturing the cosmetics based on at least one of the user information, the skin information, and the gene/medical information (S60).

According to an embodiment, data required for calculation of the method of manufacturing the cosmetics is stored in the storage unit 19, and the control unit 11 calculates the method of manufacturing the cosmetics based on the data stored in the storage unit 19, thereby acquiring the method of manufacturing the cosmetics.

According to another embodiment, the control unit 11 may transmit the user information and the skin information to the cosmetic manufacturing system 2. The cosmetic manufacturing system 2 may calculate the method of manufacturing the cosmetics based on at least one of the user information and the skin information received from the terminal 1 and the gene/medical information received from the gene/medical information server 8. In this case, the terminal 1 may acquire the method of manufacturing the cosmetics by receiving the method of manufacturing the cosmetics from the cosmetic manufacturing system 2.

Hereinafter, it is assumed that the cosmetic manufacturing system 2 calculates the method of manufacturing the cosmetics based on at least one of the user information, the genetic/medical information, and the skin information. In this case, that the cosmetic manufacturing system 2 calculates the method of manufacturing the cosmetics refers that at least one of the cosmetic manufacturing device 3 or the cosmetic manufacturing server 4 calculates the method of manufacturing the cosmetics.

The cosmetic manufacturing system 2 may select a cosmetic material to be discharged based on at least one of the user information, the genetic/medical information, and the skin information.

According to an embodiment, the cosmetic manufacturing system 2 may determine the skin of the user as any one of preset skin groups based on the genetic information and may select the cosmetic material to be discharged based on the determined skin group.

Specifically, as shown in Table 1 below, the cosmetic manufacturing system 2 may store data in which a skin group classified according to skin characteristics and a related gene for predicting the skin characteristic is mapped. Therefore, the cosmetic manufacturing system 2 acquires the genetic information related to the skin characteristics possessed by the user based on the genetic information of the user and extracts the skin group mapped to the genetic information related to the skin characteristics possessed by the user, so that the cosmetic manufacturing system 2 may determine the skin of the user as one of the preset skin groups. For example, the cosmetic manufacturing system 2 may determine the skin of the user as a group with high pigmentation/a group with dark skin color when the user has one or more of genetic mutations in the BNC2 gene based on the genetic information of the user, and may determine the skin of the user as a group with many wrinkles when the user has one or more of the genetic mutations in the AHR gene based on the genetic information of the user.

TABLE 1

| Classification by skin characteristics | Gene related to skin characteristics |
|---|---|
| Group with high pigmentation/ Group with dark skin color | BNC2<br>MC1R<br>PPARGC1B<br>MFSD12<br>FANCA<br>RAB32 |
| Group with many wrinkles | AHR<br>COL1A2<br>MMP1<br>SHC4<br>STXBP5L |

In addition, as shown in Table 2 below, the cosmetic manufacturing system 2 may store data in which the skin group classified according to skin characteristics and customized ingredients suitable for each skin group are mapped. Therefore, the cosmetic manufacturing system 2 may determine the skin group based on the genetic information and may select the customized ingredients suitable for the determined skin group as the cosmetic material to be discharged. As shown in Table 2, the customized ingredients according to the skin group may be acquired through a cell experiment or the like.

TABLE 2

| Classification by skin characteristics | Customized ingredients |
|---|---|
| Group with high pigmentation/ Group with dark skin color | Niacinamide<br>Arbutin<br>Ethyl ascorbyl ether<br>Magnesium ascorbyl phosphate<br>Ascorbyl-2-Glucoside<br>Ascorbyl tetra palmitate<br>Alpha bisabolol |
| Group with many wrinkles | Adenosine<br>Retinol<br>Polyethoxylated retinamide<br>Retinyl palmitate |

In this case, the cosmetic manufacturing system 2 may differently select the cosmetic material to be discharged according to the genetic information even though the skin information is the same or similar. For example, even though the skin information of a first user and a second user is the same or similar, the cosmetic manufacturing system 2 may select a first material as select the cosmetic material to be discharged when the first user has one or more of the genetic mutations in a first gene, and may select a second material as the cosmetic material to be discharged instead of the first material when the first user does not have one or more of the genetic mutations in the first gene. Meanwhile, the cosmetic manufacturing system 2 may classify into a group with high pigmentation/a group with dark skin color using the genetic information, and further, may discharge selecting and combining ingredients that are a particularly effective when they are caused by the genetic information among ingredients having the same efficacy. That is, even though a group for each of skin characteristics of the third user and the fourth user determined based on the genetic information is the same, when having one or more of the genetic mutations in a third gene, the cosmetic manufacturing system 2 may prescribe a third ingredient (e.g., niacinamide) among the customized ingredients (e.g., seven ingredients in Table 2 above), and when having one or more of the genetic mutations in a fourth gene, the cosmetic manufacturing system 2 may prescribe a fourth ingredient (e.g., arbutin) among the customized ingredients.

Meanwhile, Tables 1 and 2 described above are merely illustrative, and thus the present disclosure is not limited thereto. For example, in Tables 1 and 2, only the group with high pigmentation/the group with dark skin color and the group with many wrinkles are described as skin groups classified by the skin characteristics, but the skin groups classified by the skin characteristics may be various groups such as a group weak to ultraviolet rays, a group with acne-prone skin, a group with dry (keratinous) skin, and a group with sensitive skin, etc.

According to another embodiment, the cosmetic manufacturing system 2 may determine the skin of the user as any one of the preset skin groups in consideration of a preset priority among the user information, the genetic information, and the skin information, and may select the cosmetic material to be discharged based on the determined skin group.

In this case, the priority may be set as a default or may be arbitrarily set by the user.

For example, in the cosmetic manufacturing system 2, the skin information may be set as the first priority and the genetic information may be set as the second priority in the priority of skin group classification. In this case, the cosmetic manufacturing system 2 may store data in which skin information and skin groups classified by the skin characteristics are mapped as shown in Table 3 below and data in which skin subgroups classified according to genetic information are mapped within skin groups as shown in Table 4 below. The cosmetic manufacturing system 2 may determine the skin of the user as one of the preset skin groups based on the skin information using the data as shown in Table 3, and may classify the skin of the user into subgroups according to the genetic information within the skin group determined using the data as shown in Table 4.

TABLE 3

| Classification by skin characteristics | Skin information |
|---|---|
| Group with acne-prone skin | Skin color A<br>Less than 10% pigmentation |
| Group weak to ultraviolet rays | Skin color B<br>Pigmentation 10% or more |

TABLE 4

| Skin group | Subgroup | Gene related to skin characteristics |
|---|---|---|
| Group with acne-prone skin | Group with low pigmentation | BNC2<br>MC1R<br>PPARGC1B<br>MFSD12 |
| | Group with many wrinkles | FANCA<br>RAB32<br>AHR |
| Group weak to ultraviolet rays | Group with low pigmentation | COL1A2<br>MMP1 |
| | Group with many wrinkles | SHC4<br>STXBP5L |

Then, the cosmetic manufacturing system 2 may determine the cosmetic material according to the subgroup determined by the skin of the user. In addition, the cosmetic manufacturing system 2 may determine and/or correct a compounding ratio of the cosmetic material based on the user information (e.g., survey information). Meanwhile, the above-described priority is merely illustrative, and thus the present disclosure is not limited thereto.

However, as described above, when the skin information is set as the first priority and the genetic information is set as the second priority of skin group classification and the compounding ratio of the cosmetic material is corrected according to the survey information, there is an advantage that it is possible to provide the customized cosmetics by more accurately classifying the skin group of the user. Specifically, since genes are innate, the genes affect the skin of the user, but even with the same genetic information, it is almost clear that the skin varies depending on the environment in which it has been lived, and the skin group is first classified according to the skin information, then the skin subgroup is determined according to the genetic information, and then the cosmetic material is selected in consideration of the lifestyle, etc. through the survey information, and thus there is an advantage that it is possible to provide more accurately the cosmetics suitable for the skin of the user.

Likewise, Tables 3 and 4 described above are merely illustrative, and thus the present disclosure is not limited thereto.

Meanwhile, the priority is not limited to the described above. For example, the cosmetic manufacturing system 2 may classify the skin group with the genetic information as the first priority and the skin group with the skin information as the second priority, and may correct the compounding ratio of the cosmetic material according to the survey information.

Meanwhile, the cosmetic manufacturing system 2 may calculate the method of manufacturing the cosmetics by varying the order of using each of the user information, the genetic information, and the skin information, or the type and/or number of information used in the manufacture of cosmetics according to whether the cosmetic manufacturing device 1 is for a store or home use.

For example, it is assumed that the cosmetic manufacturing system 2 acquires a 34-year-old Asian woman of yellow race and a lot of outdoor activities and eating a lot of meat as the user information, acquires a lot of pigmentation but few wrinkles as the skin information, and acquires genetic information related to a lot of pigmentation and a lot of wrinkles as the genetic information.

In this case, when the cosmetic manufacturing device 1 is for store use produces a multi-dose basic product), the cosmetic manufacturing system 2 may calculate a method of manufacturing cosmetics in which the cosmetic material that supplements pigmentation and the cosmetic material that improves wrinkles are discharged in a 2:1 ratio.

Meanwhile, for the same user, when the cosmetic manufacturing device 1 is for home use (produces a single-dose basic product), the cosmetic manufacturing system 2 may calculate a method of manufacturing cosmetics by further considering the environmental information received from the environmental information server 7 in addition to the user information, the genetic information, and the skin information receives from the environmental information server 7 in addition to user information, genetic information and skin information. For example, when the cosmetic manufacturing device 1 acquires a lot of ultraviolet rays as the environmental information and acquires outdoor activities in the morning as the schedule information, the cosmetic manufacturing system 2 may calculate a method of manufacturing cosmetics in which a cosmetic material that supplements pigmentation, a cosmetic material that improves wrinkles, and a sunscreen are discharged in a 2:1:1 ratio in the morning time, and may calculate a method of manufacturing cosmetics in which the cosmetic material that supplements pigmentation, the cosmetic material that improves wrinkles, and a moisturizing cream are discharged in a 2:1:1 ratio in the afternoon time Meanwhile, the above-described cosmetic manufacturing method is merely illustrative for convenience of description, and thus the present disclosure is not limited thereto.

The control unit 11 may display cosmetic manufacturing information (S70).

The control unit 11 may display the cosmetic manufacturing information according to the method of manufacturing the cosmetics.

The cosmetic manufacturing information may refer to information on cosmetics to be manufactured, information on variables (e.g., user information, skin information, gene/medical information) that have influenced the cosmetics to be manufactured, and the like.

Next, various examples of a method of displaying the cosmetic manufacturing information by the terminal according to the embodiment of the present disclosure will be described with reference to FIGS. 10 to 13.

Figure 10:
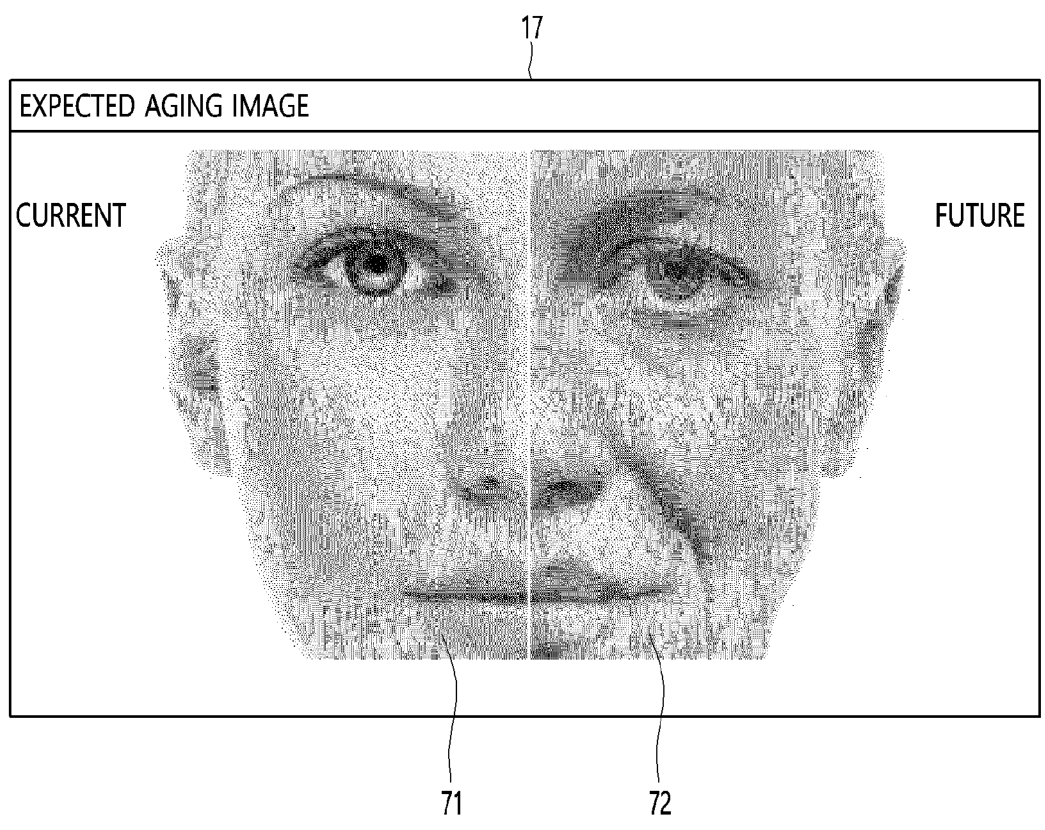
FIG. 10 is a first exemplary view of a method for the terminal according to the embodiment of the present disclosure to display a predicted aging image.

FIG. 10 is a first exemplary view of a method for the terminal according to the embodiment of the present disclosure to display a predicted aging image.

The terminal 1 may control the display unit 17 to display the predicted aging image derived based on the genetic information. Referring to an example shown in FIG. 10, the display unit 17 may display a current image 71 and a future image 72, and the current image 71 may be an image captured by the camera unit 12., and the future image 72 may be a predicted aging image derived based on the current image and the genetic information.

The future image 72 may be a predicted aging image after N years derived based on the genetic information, where N may be selected by the user.

In this case, since the terminal 1 displays the predicted aging image derived based on the genetic information, there is an advantage that it is possible to provide more accurately the predicted aging image of the user.

Figure 11:
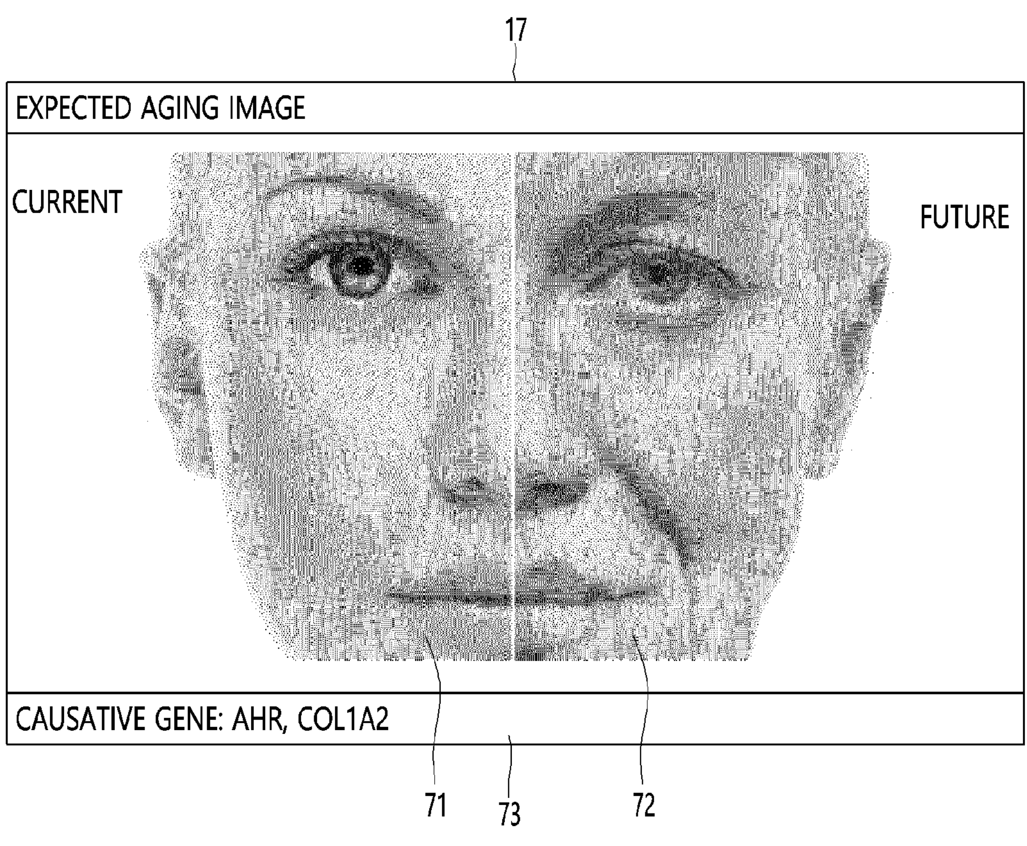
FIG. 11 is a second exemplary view of the method for the terminal according to the embodiment of the present disclosure to display the predicted aging image.

FIG. 11 is a second exemplary view of the method for the terminal according to the embodiment of the present disclosure to display the predicted aging image.

The terminal 1 may control the display unit 17 to display the predicted aging image and a causative gene derived based on the genetic information. Referring to an example shown in FIG. 11, the display unit 17 may display the current image 71, the future image 72, and a causative gene 73, and the current image 71 and the future image 72 may be as described with reference to FIG. 11. The causative gene 73 may include a predetermined number of genetic information that has an influence on future image derivation.

In this case, there is an advantage that the terminal 1 may provide not only a more accurate expected aging image but also cause information to the user.

According to the embodiment, when the customized cosmetics proposed by the present invention are used, a future image with improved skin aging may be displayed together. As a specific example, the terminal 1 may display an expected image (not shown) when cosmetics made of a cosmetic material selected based on at least one of the user information, the genetic information, and the skin information are used together with the future image 72 on the display unit 17.

FIG. 12 is an exemplary view of a method for the terminal according to the embodiment of the present disclosure to display a selected cosmetic material and genetic information related to the selected cosmetic material.

The terminal 1 may control the display unit 17 to display a cosmetic material selected to be discharged during manufacturing cosmetics and the genetic information related to the selected cosmetic material. Referring to an example shown in FIG. 12, the display unit 17 may display a cosmetic material 81 to be discharged and related genetic information 82. The discharged cosmetic material 81 may indicate a cosmetic material selected to be discharged during manufacturing cosmetics, and the related genetic information 82 may indicate cause genetic information of each of the cosmetic materials selected to be discharged. Each of the cosmetic materials 81 to be discharged may be mapped to each of the related genetic information. In an example of FIG. 12, the first material is a cosmetic material selected to be discharged by MC1R in the genetic information, the second material may be a cosmetic material selected to be discharged by FAMCA in the genetic information, a third material may be a cosmetic material selected to be discharged by SHC4 in the genetic information, and a fourth material may be a cosmetic material selected to be discharged by STXBP5L in the genetic information, but this is merely illustrative, and thus the present disclosure is not limited thereto.

FIG. 13 is an exemplary view a method for the terminal according to the embodiment of the present disclosure to display a selected cosmetic material, variable information of the selected cosmetic material, and price information of the cosmetic material.

The terminal 1 may control the display unit 17 to display at least one of the cosmetic material selected to be discharged during manufacturing cosmetics, the variable information of the selected cosmetic material, and the price information of the cosmetic material.

Referring to the example of FIG. 13, the display unit 17 may display the cosmetic material 81 to be discharged, related variable information 82, and price information 83. The discharged cosmetic material 81 may indicate a cosmetic material selected to be discharged during cosmetic manufacturing, the related variable information 82 may indicate cause information of each of the cosmetic materials selected to be discharged, and the cause information may include the user information, the skin information, the genetic information, or the like. In an example of FIG. 13, wrinkles, pigmentation, and whitening are illustrated as the cause information for which each cosmetic material is selected, and each of wrinkles, pigmentation, and whitening may be determined by the user information, the skin information, or the genetic information. The price information 83 may refer to a price of the cosmetic material to be discharged.

In this case, the terminal 1 may provide the user with each of the cosmetic materials discharged during manufacturing the cosmetics, the reason why the corresponding cosmetic material is discharged, and the price.

Meanwhile, the display unit 17 may further display a change icon 84 in addition to the cosmetic material 81 to be discharged, the related variable information 82, and the price information 83.

In this case, the control unit 11 may receive a command to change the cosmetic material to be discharged through a selection command of the change icon 84, and accordingly the control unit 11 may change the cosmetic material to be discharged.

In this case, there is an advantage that the terminal 1 provides a function in which the user may change at least one cosmetic material based on each of the cosmetic materials discharged during manufacturing the cosmetics, the reason why the corresponding cosmetic material is discharged, and the price.

Meanwhile, according to another embodiment of the present disclosure, the system for providing customized cosmetics may diagnose a skin condition based on skin glycation information together with genetic information and recommend customized cosmetics or a health functional food.

According to still another embodiment of the present disclosure, the system for providing customized cosmetics may diagnose the skin condition based on only the skin glycation information and recommend the customized cosmetics or the health functional food.

That is, the system for providing customized cosmetics according to the present disclosure may diagnose the skin condition based on at least one of the genetic information and the skin glycation information and recommend the customized cosmetics or the health functional food.

Therefore, a method based on the skin glycation information when diagnosing the skin condition and recommending the customized cosmetics or the health functional food will be described in more detail below.

The system for providing customized cosmetics may non-invasively analyze a skin aging index based on the skin glycation information of the user and recommend optimal or customized cosmetics or the health functional food based on this.

Advanced glycation end products (AGEs) accumulated in the skin are known to cause various skin aging phenomena such as increased wrinkles, decreased elasticity, and dry skin.

The advanced glycation end products (AGEs) accumulated in the skin may be measured through an invasive method such as skin biopsy, a method using autofluorescence, a non-invasive method, and the like.

The embodiment intends to provide a skin condition diagnosis system based on the skin glycation information and a recommendation system based on the skin glycation information using the same by non-invasively evaluating the advanced glycation end products of the skin of the user.

In particular, the embodiment intends to provide the skin condition diagnosis system that may analyze a degree of glycation accumulation for each region of the user's face in detail and effectively display the degree of glycation accumulation for each region and the recommendation system based on the skin glycation information.

In addition, the embodiment intends to provide the skin condition diagnosis system that may study the correlation between the skin condition of the user and a skin glycation measurement value using a non-invasive autofluorescence skin glycation measurement device and may provide a skin aging index analysis method according to the skin glycation measurement value based on accumulated data and the recommendation system based on the skin glycation information.

In addition, the embodiment intends to provide the skin condition diagnosis system that may provide to the user by analyzing the glycation product decomposition efficacy of products having a function of inhibiting and decomposing skin glycation products and making a list of recommended products and the recommendation system based on the skin glycation information.

Hereinafter, the customized cosmetics may refer to cosmetics provided by mixing and selling immediately between final products or as final products+raw materials according to needs of consumers in a store.

The customized cosmetics may include cosmetics obtained by adding and mixing contents of other cosmetics or raw materials prescribed by the director of food and drug administration (FDA) to contents of manufactured/imported cosmetics, and cosmetics obtained by subdividing the contents of manufactured/imported cosmetics.

Therefore, it is possible to provide the customized cosmetics or the health functional foods by recommending and mixing products that may objectively diagnose the skin type of the user and accurately care for concerns. For example, it is possible to provide a total of 30 recipes by selecting 1 out of 3 serums and 2 out of 5 ampoules.

A process for providing customized cosmetics may be as follows.

Step 1: Interview

Confirm lifestyle and skin concerns through interviews

Step 2: Precision Analysis

Precisely analyze skin condition and skin concerns with a facial inspection machine Step 3: Counseling Recommend 1:1 customized recipe through skin analysis and counseling Step 4: Mix Products Mix safely with a final recipe and complete the product with unique labeling The embodiment may study the skin characteristics of the user based on the skin glycation information and provide the optimal or customized cosmetics or the health functional food based on the skin glycation information of the user.

Figure 14:
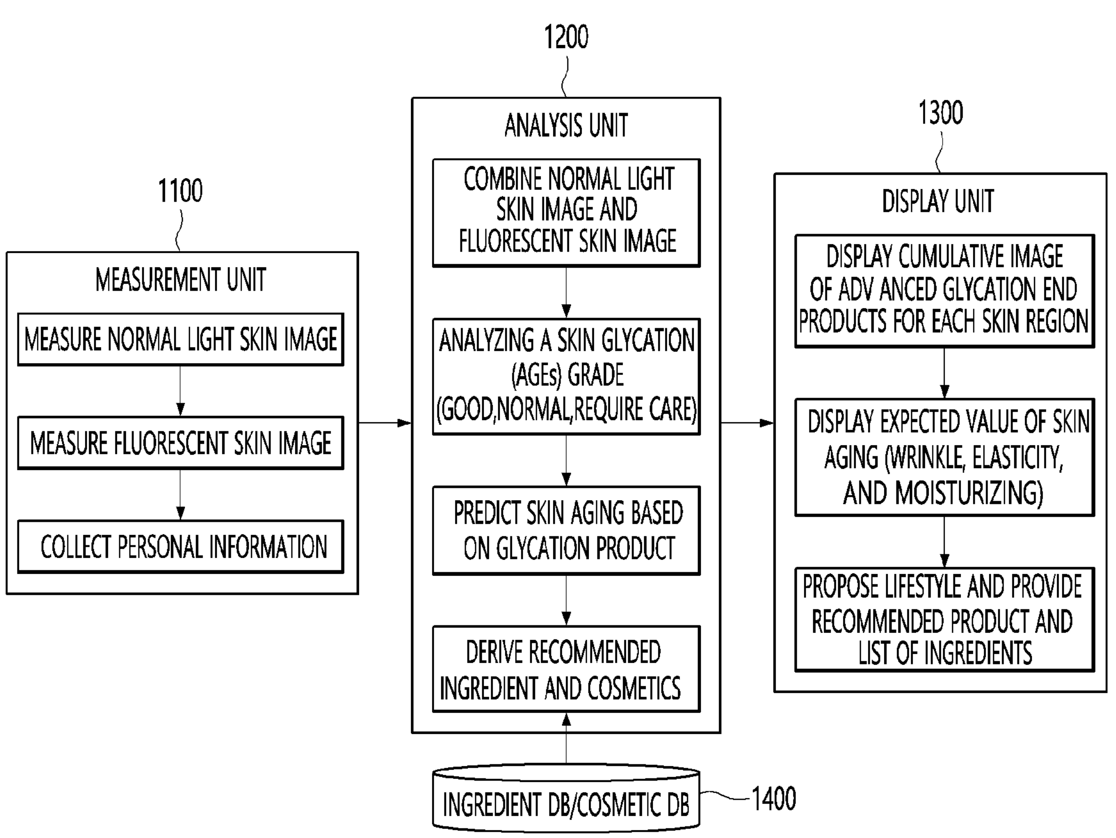
FIG. 14 is a block diagram of a skin condition diagnosis system 1000 based on skin glycation information according to an embodiment.

First, FIG. 14 is a block diagram of a skin condition diagnosis system 1000 based on skin glycation information according to an embodiment.

The skin condition diagnosis system 1000 shown in FIG. 14 may be a part of the system for providing customized cosmetics described in FIG. 1.

The skin condition diagnosis system 1000 based on the skin glycation information according to the embodiment may include a measurement unit 1100, an analysis unit 1200, and a display unit 1300. In addition, the embodiment may include a database 1400, for example, an ingredient database, and a cosmetic database.

According to the embodiment, it is possible to study the correlation between the skin condition of the user and the skin glycation measurement value using the non-invasive autofluorescence skin glycation measurement device, and to develop the skin aging index analysis method according to the skin glycation value measured based on the accumulated data.

For example, according to the embodiment, it is possible to study the correlation between wrinkles, elasticity, moisture of the customer and the skin glycation measurement value using the non-invasive autofluorescence skin glycation measurement device, and to develop a skin aging index analysis algorithm according to the skin glycation measurement value based on the accumulated data.

In addition, according to the embodiment, by analyzing the glycation product decomposition efficacy of products having the function of inhibiting and decomposing skin glycation products, it is possible to create a list of recommended products and recommend them to the user through the system.

For example, according to the embodiment, it is possible to provide a method capable of recommending a list of products having the effect of decomposing and inhibiting the glycation end products (AGEs) to consumers by constructing a human efficacy evaluation system for products having the function of inhibiting and decomposing the skin glycation products.

According to the embodiment, it is possible to measure the advanced glycation end products (AGEs) accumulated in the skin of the user through a non-invasive autofluorescence detection method, to diagnose a skin aging level based on a skin glycation level of the user, and to recommend cosmetics or health functional foods that may suppress skin glycation and skin aging.

Referring to FIG. 14, in the embodiment, the measurement unit 1100 may perform a step of measuring a normal light skin image, a step of measuring a fluorescent skin image, and a step of collecting personal information.

In the embodiment, the measurement unit 1100 may use the non-invasive autofluorescence detection method.

Referring to FIG. 14, in the embodiment, the analysis unit 1200 may include a step of combining the normal light skin image and the fluorescent skin image, a step of analyzing a skin glycation (AGEs) grade (good, normal, requires care, etc.), a step of predicting skin aging based on the glycation product, a step of deriving recommended ingredients and cosmetics based on the ingredient database and the cosmetic database.

Referring to FIG. 14, in the embodiment, the display unit 1300 may serve a function of displaying the cumulative image of the advanced glycation end products for each skin region, a function of displaying an expected value of skin aging (wrinkle, elasticity, and moisturizing), a function of proposing a lifestyle, and a function of providing a recommended product and a list of ingredients.

Figure 15:
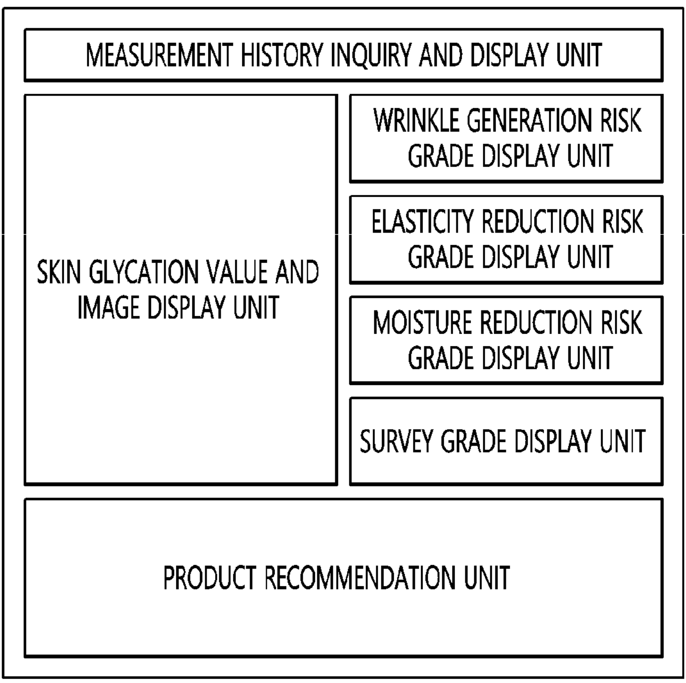
FIG. 15 is a detailed view of a display unit 1300 in the skin condition diagnosis system based on the skin glycation information according to the embodiment shown in FIG. 14.

Specifically, FIG. 15 is a detailed view of the display unit 1300 in the skin condition diagnosis system based on the skin glycation information according to the embodiment shown in FIG. 14.

Referring to FIG. 15, in the embodiment, the display unit 1300 may include a measurement history inquiry and display unit, a skin glycation value and image display unit, a wrinkle generation risk grade display unit, an elasticity reduction risk grade display unit, a moisture reduction risk grade display unit, and a survey grade display unit, a product recommendation unit, and the like.

For example, referring to FIG. 15, in the display unit 1300 of the embodiment, the ‘wrinkle generation risk grade display unit’ may display a cumulative skin glycation value in a region of forehead, around eyes, under eyes, and laugh lines divided into three grades (low/normal/high) in consideration of age group and gender.

In addition, in the display unit 1300 of the embodiment, the ‘elasticity reduction risk grade display unit’ may display a cumulative skin glycation value in a cheek region divided into three grades (low/normal/high) in consideration of age group and gender.

In addition, in the display unit 1300 of the embodiment, the ‘moisture reduction risk grade display unit’ may display an average cumulative skin glycation value in the entire face divided into three grades (low/normal/high) in consideration of age group and gender.

In addition, in the display unit 1300 of the embodiment, the ‘survey grade display unit’ may provide UV exposure habit and sugar intake habit grade (good/normal//requires care), and when the grade is normal or/requires care, it is possible to provide a detailed content on lifestyle improvement measures.

The display unit 1300 of the embodiment may provide information so that the user may compare changes in the skin glycation products through comparison with existing measurement information by providing a button capable of inquiring previously measured data.

As described above, the related art focuses on improving the possibility of overall health diagnosis related to diabetes by measuring the glycation products (AGEs) of the human skin with autofluorescence, and there is a lack of research on a technology that may analyze a degree of glycation accumulation for each region of the face in detail and effectively display the degree of glycation accumulation for each region of the face.

Accordingly, one of technical tasks of the embodiment is to provide a skin condition diagnosis system that may analyze the degree of glycation accumulation for each region of the face of the user in detail and effectively display the degree of glycation accumulation for each region.

Figure 16:
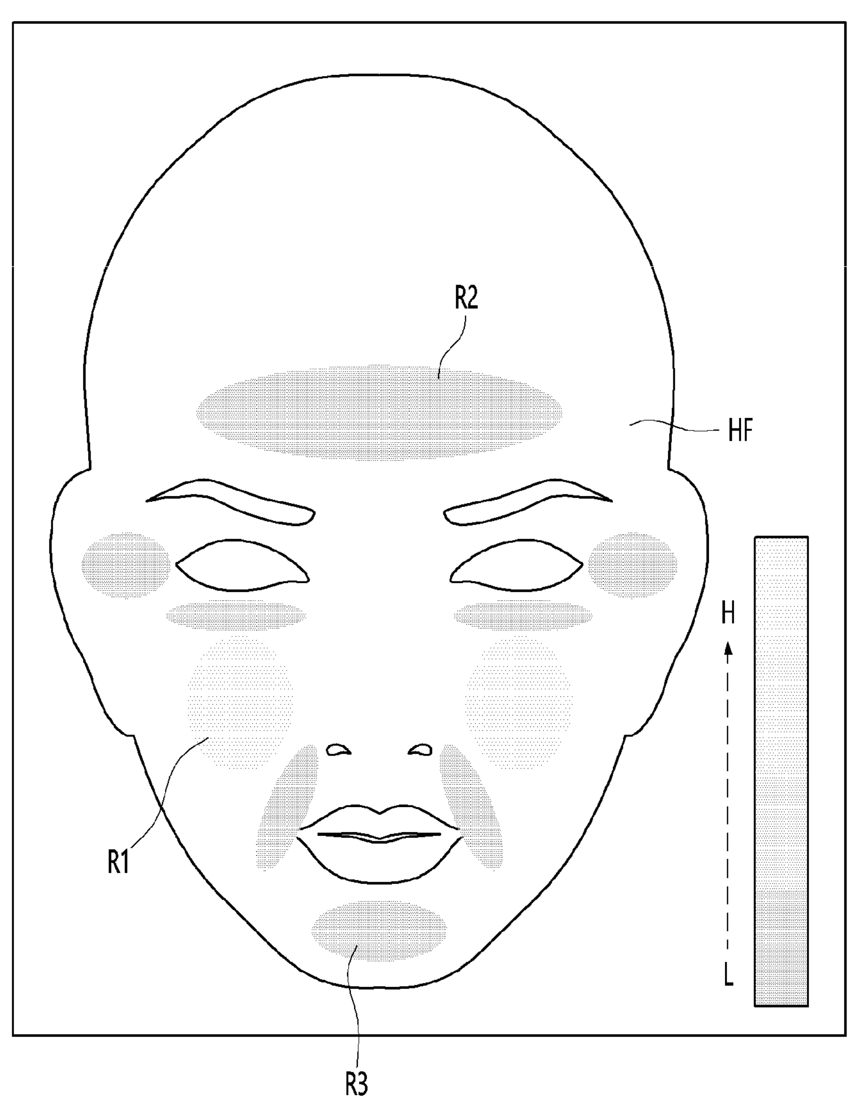
FIG. 16 is an exemplary view for displaying an image of a skin glycation value on the display unit 1300 in the skin condition diagnosis system shown in FIG. 15.

FIG. 16 is an exemplary view displaying an image of a skin glycation value on the display unit 1300 in the skin condition diagnosis system shown in FIG. 15.

According to the embodiment, the skin glycation value on the display unit 1300 is overlaid by converting the degree of glycation accumulation for each region into color change on the general light skin image, and as the glycation value is increased, the color is adjusted from red to green to display, so that consumers may easily understand. In the embodiment, an image for measuring the degree of glycation may be sensed by the non-invasive autofluorescence detection method while turning on/off an UV LED, but the present disclosure is not limited thereto.

The embodiment has a technical effect that it is possible to provide the skin condition diagnosis system that may analyze the degree of glycation accumulation for each region of the face of the user in detail and effectively display the degree of glycation accumulation for each region of the face of the user. In the embodiment, detailed analysis of the degree of glycation accumulation for each region of the face in the user's body and the diagnosis of the skin condition for each region are described, but the present disclosure is not limited thereto. The embodiment may also be applied to detailed analysis of the degree of glycation accumulation and diagnosis of skin condition for each region of other body parts, such as arms, of the user's body.

For example, FIG. 16 is an exemplary view showing that a cheek region R1 has a high glycation value in a facial skin HF of the user, while a forehead region R2 and a chin region R3 have relatively low glycation values.

In the embodiment, a skin glycation level may be divided into a facial region (forehead, nose, around left eye, under left eye, around right eye, under right eye, left cheek, right cheek, left laugh line, right laugh line, blow, chin) score and an overall average score based on a measured fluorescence intensity.

In the embodiment, an overall average score for facial skin glycation may be calculated through an average of the measurement scores for each region, and may have a weight in consideration of an area and importance of a measurement region.

Hereinafter, a method of measuring and analyzing skin glycation in the skin condition diagnosis system according to the embodiment will be described in more detail.

First, in the embodiment, a first step of exposing a first skin region to a first exposure light may be performed so that the first skin region of the facial skin of the user emits reflected light in a visible ray region, and the first exposure light may include a light source emitting white light.

Next, a second step of capturing the reflected light in the visible ray region with a camera of a detection unit, for example, a DSLR camera may be performed.

Next, a third step of exposing the first skin region to excitation light for exposing the first skin region to a second light source may be performed so that the personal facial skin of the user emits fluorescence, and the second light source may include a UV wavelength of 340 nm to 400 nm Next, a fourth step of selecting emitted light of about 430 nm to 450 nm through a fluorescence control filter of a switching control unit and capturing the emitted light with the camera of the detection unit may be performed.

Next, a fifth step of selecting the same region of region of image (ROI) of images measured in the second step and the fourth step in a calculation unit and calculating skin reflection light intensity ($I_V$) of the second step and fluorescence emission intensity ($I_{UV}$) of the fourth step may be performed.

Next, a sixth step of calculating (refer to Equation 1) a fluorescence emission light intensity (AF) using the fluorescence emission light intensity ($I_{UV}$) of the fourth step and the fifth stage skin reflected light measurement intensity ($I_V$) of the fifth step in order to correct the fluorescence emission light intensity for the skin color in the calculation unit may be performed.

$$AF=\langle I_{UV}\rangle-(\alpha\times\langle I_V\rangle+\beta) \quad \text{[Equation 1]}$$

($\alpha$, $\beta$ values are calculated values acquired by linear regression of the correlation between the skin measurement data of the second and fourth steps, and according to a measurement position of the user's face such as forehead, cheek, eye region, under the eyes, and arms, $\alpha$, $\beta$ values may be $0\leq\alpha\leq22$, $0\leq\beta\leq255$, preferably $0\leq\alpha\leq10$, $0\leq\beta\leq200$, and more preferably $1\leq\alpha\leq2$, $0\leq\beta\leq150$, but the present disclosure is not limited thereto.)

Figure 18:
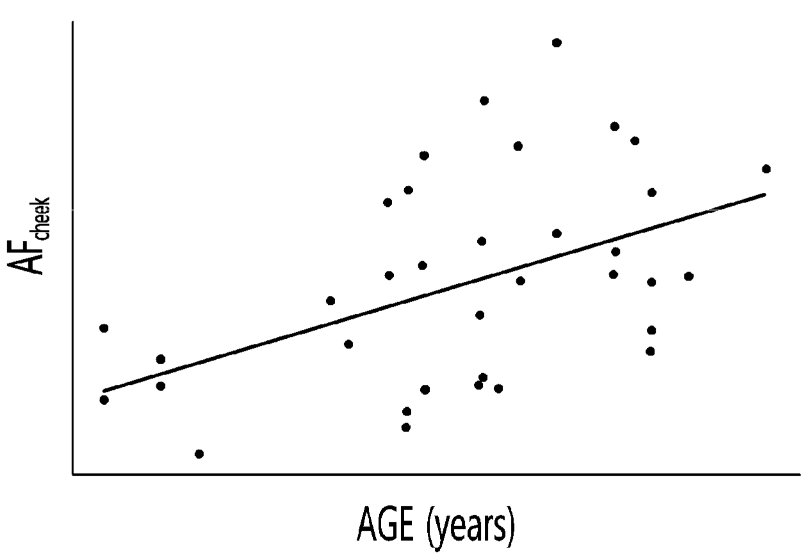
FIG. 18 is data on a correlation between a fluorescence emission light intensity (AF) corrected in a sixth step and a subject's age (AGE).

Next, a seventh step of calculating a skin aging risk degree by plotting the fluorescence emission light intensity (AF) corrected in the sixth step on a standard curve for individual age may be performed. For example, the risk degree may be calculated as good for less than an upper criterion, normal for more than the upper criterion and less than an average, and management required for more than the average and less than a lower criterion. For example, FIG. 18 is data on a correlation between the fluorescence emission light intensity (AF) corrected in the sixth step and a subject's age (AGE). Based on such an age and fluorescence emission intensity data, it is possible to effectively confirm how much glycation has progressed compared to the age by comparing a subject's age inversely calculated through the measured AF value with a subject's own age.

Referring to FIGS. 16 and 15, the fluorescence emission light intensity (AF) for each region is effectively derived through a method of measuring and analyzing the skin glycation in the skin condition diagnosis system described above for the cheek region R1, the forehead region R2, and the chin region R3 of the user's facial skin HF, and according to such information, the display unit 1300 in the skin condition diagnosis system of the embodiment converts the glycation accumulation level for each region into a color change and overlays it to display as a color image, so that there is a special technical effect that it is possible to provide the skin condition diagnosis system that may effectively analyze and display the degree of glycation accumulation for each region.

In addition, according to the embodiment, the calculation unit performs the sixth step of calculating the fluorescence emission light intensity AF by correcting the fluorescence emission light intensity ($I_{UV}$) in the fourth step (refer to Equation 1). In this case, the fluorescence emission light intensity (AF) is corrected in consideration of the characteristics for each region of the skin to accurately calculate and display as a color image by overlaying the AF, so that there is a special technical effect that it is possible to provide the skin condition diagnosis system that may accurately and effectively analyze and display the degree of glycation accumulation for each region.

On the other hand, the related art focuses on improving the possibility of overall health diagnosis related to diabetes by measuring the glycation products (AGEs) of the human skin with autofluorescence, and there is a lack of research on a technology that may analyze a degree of glycation accumulation for each region of the face in detail and effectively display the degree of glycation accumulation for each region of the face.

Figure 17:
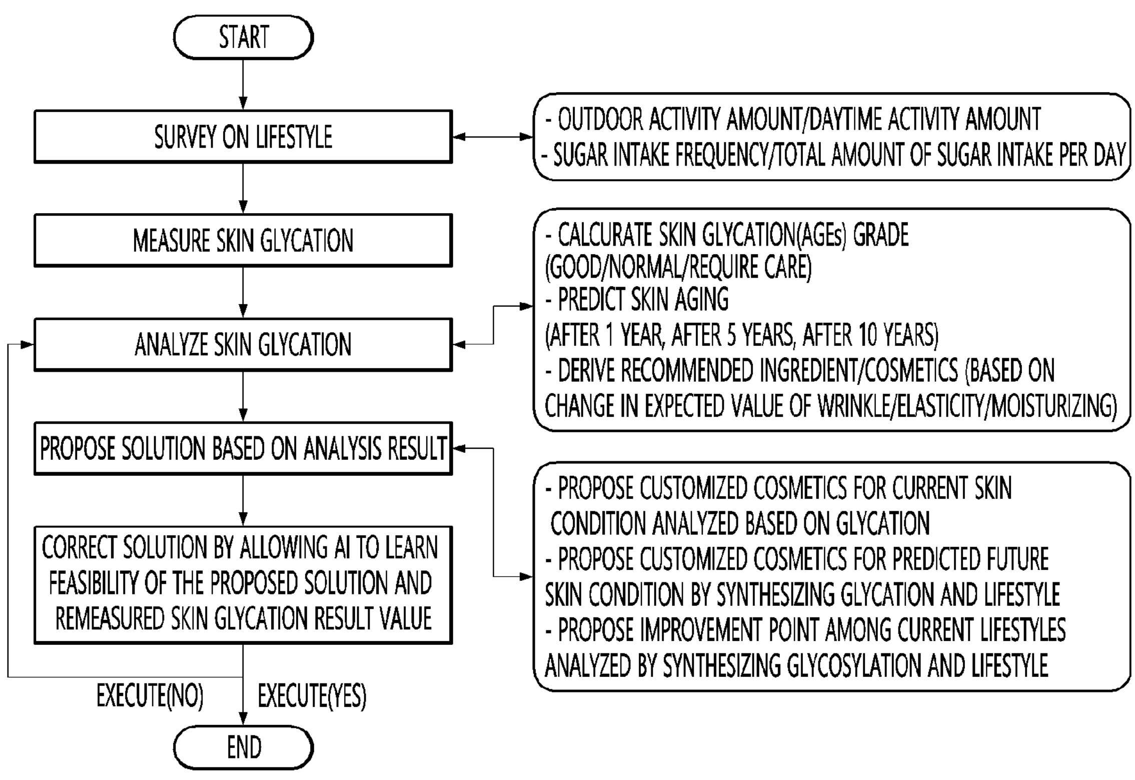
FIG. 17 is an exemplary view of an algorithm for recommending a product group suitable for a user based on the skin condition diagnosis system based on the skin glycation information according to the embodiment shown in FIG. 14 and a recommendation system based on the skin glycation information using the same.

Next, FIG. 17 is an exemplary view of an algorithm for recommending a product group suitable for the user based on the skin condition diagnosis system based on the skin glycation information according to the embodiment shown in FIG. 14 and the recommendation system based on the skin glycation information using the same.

First, according to the embodiment, it is possible to conduct a survey on the user's lifestyle.

For example, it is possible to conduct a survey of outdoor activity amount, daytime activity amount, sugar intake frequency, total amount of sugar intake per day of the user, and the like.

In the embodiment, the user's UV exposure habit and sugar intake habit may be classified into three grades (good/normal/requires care) based on a survey response.

Accordingly, in the embodiment, the product recommendation method may provide accurate information by synthesizing the user's personal information (age, gender, type of product used, sugar intake habit, UV exposure habit) acquired through the survey and the overall average score of facial skin glycation.

For example, according to the embodiment, a lifestyle survey regarding exercise, smoking, drinking, sleeping time, stress, eating habits, etc. related to the skin glycation index may be conducted as shown in Table 5 below, but the present disclosure is not limited thereto (exercise may refer to walking for 30 minutes or more or equivalent level).

TABLE 5

| | Score | | | | |
|---|---|---|---|---|---|
| Item | 1 | 2 | 3 | 4 | 5 |
| How often do you exercise? | Not do at all | Daily exercise at home or in office | Once a week | 2 or 3 times a week | 4 or more times a week |
| Do you smoke? | Smoking every day for more than 10 years | Smoking for more than 1 year | Non-smoking | | |
| Do you drink? | 4 or more times a week | 2~3 times a week | Once a week | Less than once a week | Not drinking |
| How many hours do you sleep a day? | Less than 4 hours | 4~5 hours | 5~7 hours | 7~8 hours | 8 hours or more |
| Are you feeling any mental stress? | Very so | yes | I do not know | Not so | Not very so |
| Do you eat vegetables? | Not very so | Not so | I do not know | yes | Very so |
| Do you have breakfast every day? | Not very so | Not so | I do not know | yes | Very so |
| Do you eat moderately so that you don't feel full? (Until 80% full) | Not very so | Not so | I do not know | yes | Very so |
| Do you try to eat less fatty food? | Not very so | Not so | I do not know | yes | Very so |
| Do you try to eat less processed food? | Not very so | Not so | I do not know | yes | Very so |
| Do you try not to eat sweets like cake or candy? | Not very so | Not so | I do not know | yes | Very so |

Next, in the embodiment, it is possible to measure and analyze the skin glycation of the user. In the embodiment, skin glycation measurement information of the user may be classified into three grades (good/normal/requires care) in consideration of age and gender.

Next, the embodiment may propose a solution based on the analysis result. For example, the embodiment may propose customized cosmetics or health functional foods for the current skin condition analyzed based on the glycation.

In particular, according to the embodiment, the fluorescence emission light intensity (AF) for each region is effectively derived through a method of measuring and analyzing the skin glycation in the skin condition diagnosis system described above for the cheek region R1, the forehead region R2, and the chin region R3 of the user's facial skin HF, and according to such information, the display unit 1300 in the skin condition diagnosis system of the embodiment converts the glycation accumulation level for each region into a color change and overlays it to display as a color image, so that it is possible to provide the skin condition diagnosis system that may effectively analyze and display the degree of glycation accumulation for each region, and it is possible to propose customized cosmetics or health functional foods for the skin condition for each region based on such effective analysis and effective display technology for each region.

Specifically, when the skin glycation measurement information corresponds to normal and requires care, it is possible to refer to a cosmetics DB to recommend cosmetics suitable for decomposition/inhibition of the skin glycation products, and when the UV exposure habit and the sugar intake habit correspond to normal and requires care, it is possible to provide together with a guide for improving lifestyle.

In addition, When the skin glycation measurement information corresponds to good, that it is possible to recommend cosmetics that do not includes the effect of decomposing/inhibiting the skin glycation products, and in this case, when the UV exposure habit and the sugar intake habit correspond to normal and requires care, it is possible to provide together with the guide for improving the lifestyle.

In addition, the embodiment may propose customized cosmetics for a predicted future skin condition by synthesizing the glycation and the lifestyle.

For example, the embodiment may predict skin aging (after 1 year, after 5 years, after 10 years) by synthesizing the skin glycation grade and the lifestyle and may derive recommended ingredients/cosmetics/health functional foods based on the same (based on a change in an expected value of wrinkle/elasticity/moisturizing).

For example, the embodiment may recommend the cosmetics or the health functional foods by synthesizing the skin glycation grade and the lifestyle.

For example, the embodiment may recommend cosmetics or health functional foods containing any one or two or more of (2-(1-ethoxyethoxy)ethyl)benzene ((2-(1-ethoxyethoxy) ethyl)benzene), 1,2,4-trihydroxyanthraquinone (1,2,4-trihydroxyanthraquinone), 4-(4-hydroxyphenyl)-2-butanone (4-(4-Hydroxyphenyl)-2-butanone), 6-hydroxy-7-methoxy-4-phenylcoumarin (6-hydroxy-7-methoxy-4-phenylcoumarin), 8-Gingerol, L-Asarinin, gaguja extract, kawa extract, gaultherin, pueraria extract, chrysanthemum indicum extract, chrysanthemum indicum flower extract, licorice extract, ostericum extract, turmeric extract, nonglutinous rice extract, rehmannia glutinosa extract, black bean extract, spatholobus extract, balloon flower extract, sophora extract, eriocaulon extract, trichosanthis semen extract, pogostemon extract, trichosanthis radix extract, lycium extract, chrysanthemum extract, lonicer aflower extract, platycodon extract, honey extract, narcissoside, and southern frankincense extract.

In addition, the embodiment may recommend cosmetics or health functional foods containing any one or two or more of neobavaisoflavone, nepetin, nepodin, phragmites communis extract, notopterol, antler extract, deer antlers extract, dankook extract, salvia miltiorrhiza extract, damdusi extract, angelica gigas extract, codonopsis extract, daejo extract, jujube extract, rhubarb extract, demethylbellidifolin, demethylwedelolactone, demopsoside, dehydrotomulsic acid, prunus persica extract, dohwa extract, aralia continentalis extract, dujung extract, dracorhodin perochlorate, dimethylzeylasteral, diosbulbin B, dihydrotansinone I, dictamnine, rehmapicroside, rebaudioside A, rebaudioside C, rubusoside, lithospermic acid, liquid lactone, liriopeseides B, vitex rotundifolia extract, liriope platyphylla extract, and hordeum vulgare extract.

In addition, the embodiment may recommend cosmetics or health functional foods containing any one or two or more of methylophiopogonanone A, mortierella isabellina extract, paeonia suffruticosa extract, akebia quinata extract, aucklandia lappa extract, molsikja extract, dandelion extract, babachalcone, babachinin A, bayogenin, peppermint extract, peppermint leaves extract, pinellia ternata extract, valechlorine, saposhnikovia divaricata extract, bombyx mori extract, baekajain extract, bletilla striata extract, santalum album extract, poria cocos extract, dictamnus dasycarpus extract, thuja orientalis extract, paeonia japonica extract, baekjiryeo extract, atractylodes macrocephala extract, lily extract, hedyotis diffusa extract, vomicine, poria cocos extract, spirodela polyrrhiza extract, bungal extract, bungalhwa extract, brassinolide, brucein D, brucine, and vinorelbine.

In addition, the embodiment may recommend cosmetics or health functional foods containing any one or two or more of eriobotrya japonica extract, dioscorea tokora extract, adenophora stricta extract, torilis japonica extract, cyclen, amomum villosum extract, crataegus pinnatifida extract, cornus officinalis extract, dioscorea japonica extract, zizyphus jujuba extract, sanchija extract, salinivibrio sp. extract, salvianolic acid C, panax notoginsengs extract, moms bombycis extract, raw licorice extract, ginger extract, raw ginseng extract, saengjihwang extract, dendrobium extract, seonnogeun extract, wheat extract, caesalpinia sappan extract, and rehmannia glutinosa extract.

In addition, the embodiment may recommend cosmetics or health functional foods containing any one or two or more of schisantherin A, pseudolaric acid A, pseudoprotodioscin, swertisin, strychnine, specnuezhenide., horse sericin extract, cynaroside, sinigrin, syringaresnol-4-O-β apiopuranosi, bupleurum falcatum extract, magnolia extract, anemoside A3, aristolactam I, linum usitatissimum extract, absinthiin, acetylcimigenol arabinoside, isobavachin, isoschaftoside, isosteviol, isocurcumenol, and ajugol.

In addition, the embodiment may recommend cosmetics or health functional foods containing any one or two or more of curcuma extract, alkannin, yagyodeung extract, houttuynia cordata extract, esculentoside A, ethyl ferulate, ligustrum extract, forsythia suspensa extract, yeonsil extract, yeonsim extract, nelumbo nucifera extract, lotus root extract, lysimachia foenum-graecum extract, prunus mume extract, schisandra chinensis extract, obacunone, evodia rutaecarpa extract, opilcho extract, oxypeucedanin hydrate, polygonatum odoratum extract, oleandrin, arctium lappa extract, achyranthes bidentata extract, uyu extract, prunus japonica extract, unryeong extract, polygala tenuifolia extract, wigeun extract, eupalinolide A, boswellia carterii extract, cinnamomum cassia extract, cistanche deserticola extract, and euni extract.

In addition, the embodiment may recommend cosmetics or health functional foods containing any one or two or more of isodimethylwedelolactone, isosakuranetin, ginseng extract, injin extract, aster tataricus extract, jajilyeo extract, jacho extract, jahwanggi extract, peony extract, red peony extract, syzygium aromaticum extract, genipin-1-b-D-gentiobioside, geraniin, gleditsia sinensis extract, jongyong extract, bamboo leaf extract, citrus aurantium extract, lycium chinense extract, anemarrhena asphodeloides extract, kochia scoparia extract, poncirus trifoliata extracts, borage extracts, rehmannia glutinosa extracts, citrus unshiu extracts, plantago asiatica extracts, xanthium strumarium extracts, atractylodes lancea extracts, cnidium officinale extracts, gastrodia elata extracts, chaenomeles sinensis extracts, asparagus cochinchinensis extracts, cheonhwabun extracts, chumguaja extracts, chogyeolmyung extracts, and gardenia extracts.

In addition, the embodiment may recommend cosmetics or health functional foods containing any one or two or more of caudatin, kakoul, calceolarioside B, corytuberine, curine, quercetin-3-O-sophoroside (protosappanin B), alisma orientale extract, tenuifolin, tenuifoliside A, thermopsine, tectorigenin 7-O-xylosylglucoside, tectorigenin, tectoridin, smilax glabra extract, cuscuta chinensis extract, tubeimoside B, and tussilagone, tracheloside, timosaponin A-III extract, perillartine, periplogenin, polygalasaponin F, polygalacin D, polygalaxanthone III, praeruptorin A, protosappanin B, phillygenin, prunella vulgaris extract, polygonum multiflorum extract, hasatoside, eclipta prostrata extract, halomonas sp. extract, halobacillus sp. extract, haloarcula sp. extract, haloarcula sp. extract, prunus armeniaca, hyangbuja extract, and hyangchunja extrac.

In addition, the embodiment may recommend cosmetics or health functional foods containing any one or two or more of hederacoside C, hematoxylin, scrophularia buergeriana extract, schizonepeta tenuifolia extract, juglans regia extract, trigonella extract, homoplantaginin, homoharringtonin, carthamus tinctorius extract, scutellaria baicalensis extract, astragalus membranaceus extract, coptis japonica extract, phellodendron amurense extract, Polygonatum extract, hwangjinpi extract, and hupehenin.

In addition, the embodiment may propose improvement points among current lifestyles analyzed by synthesizing the glycosylation and the lifestyle.

Next, the embodiment may allow the AI to learn the feasibility of the proposed solution and the remeasured skin glycation result value to perform a solution correction step, and the step is terminated when the solution is executed.

According to the embodiment, it is possible to study the correlation between the skin condition of the user and the skin glycation measurement value using the non-invasive autofluorescence skin glycation measurement device, and to develop the skin aging index analysis method according to the skin glycation value measured based on the accumulated data.

For example, according to the embodiment, it is possible to study the correlation between wrinkles, elasticity, moisture of the customer and the skin glycation measurement value using the non-invasive autofluorescence skin glycation measurement device, and to develop a skin aging index analysis algorithm according to the skin glycation measurement value based on the accumulated data.

In addition, according to the embodiment, by analyzing the gly cation product decomposition efficacy of products having the function of inhibiting and decomposing skin glycation products, it is possible to create a list of recommended products and recommend them to the user through the system.

For example, according to the embodiment, it is possible to provide a method capable of recommending a list of products having the effect of decomposing and inhibiting the glycation end products (AGEs) to consumers by constructing a human efficacy evaluation system for products having the function of inhibiting and decomposing the skin glycation products.

According to the embodiment, it is possible to measure the advanced glycation end products (AGEs) accumulated in the skin of the user through a non-invasive autofluorescence detection method, to diagnose a skin aging level based on a skin glycation level of the user, and to recommend cosmetics or health functional foods that may suppress skin glycation and skin aging.

The present disclosure described above may be implemented as computer-readable codes in a medium on which a program is recorded. The computer-readable medium includes all kinds of recording devices in which data readable by a computer system is stored. Examples of the computer-readable medium include a hard disk drive (HDD), a solid state disk (SSD), a silicon disk drive (SDD), a ROM, a RAM, a CD-ROM, a magnetic tape, a floppy disk, and an optical data storage, etc. In addition, the computer may include the control unit of the terminal 1 or the control unit 31 of the dispenser 3. Therefore, the above detailed description should not be construed in a limiting sense in all respects, and should be considered as examples. The scope of the present invention should be determined by rational interpretation of the appended claims, and encompasses all alterations falling within the equivalent scope of the appended claims.

The above description is merely illustrative of the technical spirit of the present invention, and various modifications and variations will be possible without departing from the essential characteristics of the present invention by those skilled in the art to which the present invention pertains.

Therefore, the embodiments disclosed in the present invention are not intended to limit the technical spirit of the present invention, but to explain, and the scope of the technical spirit of the present invention is not limited by these embodiments.

The protection scope of the present invention should be construed by the following claims, and all technical ideas within the equivalent range should be construed as being included in the scope of the present invention.

The invention claimed is:

1. A system for providing customized cosmetics, the system comprising:

a terminal that receives user information related to a user and includes a user identification unit for identifying the user;

a gene/medical information server that stores genetic information and medical information related to the user;

a skin meter that acquires skin information on the user; and a cosmetic manufacturing system including a cosmetic manufacturing server and a cosmetic manufacturing device, wherein the cosmetic manufacturing server is configured to receive the user information from the terminal, receive at least one of the genetic information or the medical information from the gene/medical information server, receive the skin information from the skin meter, and select a cosmetic material to be discharged based on at least one of the user information, the genetic information, the medical information and the skin information, wherein the cosmetic manufacturing server is further configured to transmit cosmetic information and a control signal to the cosmetic manufacturing device, wherein the cosmetic manufacturing device is configured to manufacture cosmetics by discharging at least one cosmetic material in response to the control signal, wherein the terminal further includes a user identification unit configured to identify the user, an input unit configured to receive the user information related to the identified user, and a controller configured to determine a security level based on identification information acquired when identifying the user, wherein the gene/medical information server acquires at least one of the genetic information and the medical information according to the security level, wherein the gene/medical information server is configured to acquire the genetic information when the security level is a first level, acquire the medical information when the security level is a second level, and acquire the genetic information and the medical information when the security level is a third level, and wherein the cosmetic manufacturing server is configured to select the cosmetic material to be discharged differently according to the genetic information even though the skin information is the same.

2. The system of claim 1, further comprising:

a key authentication server that shares a public key when the user is identified through the user identification unit, wherein the gene/medical information server transmits the genetic information to the cosmetic manufacturing system when receiving a server key generated based on the public key.

3. The system of claim 1, wherein the cosmetic manufacturing system determines a skin of the user as any one of preset skin groups based on the genetic information, and selects the cosmetic material to be discharged based on the determined skin group.

4. The system of claim 1, wherein the cosmetic manufacturing system determines a skin of the user as any one of preset skin groups in consideration of a preset priority among the user information, the genetic information, and the skin information and selects the cosmetic material to be discharged based on the determined skin group.

5. The system of claim 4, wherein the cosmetic manufacturing system determines a group to which the skin of the user belongs based on the skin information, and determines a subgroup to which the skin of the user belongs within the determined group using the genetic information to select the cosmetic material to be discharged.

6. The system of claim 5, wherein the terminal receives survey information as the user information, and wherein the cosmetic manufacturing system corrects a compounding ratio of the cosmetic material to be discharged that is selected based on the survey information.

7. The system of claim 1, wherein the terminal displays a predicted aging image derived based on the genetic information.

8. The system of claim 1, wherein the terminal displays genetic information related to the selected cosmetic material.

9. The system of claim 1, wherein the terminal displays at least one of the selected cosmetic material, variable information of the selected cosmetic material, and price information of the cosmetic material, and further receives an input for changing the cosmetic material.

10. The system of claim 1, wherein the cosmetic manufacturing system selects the cosmetic material to be discharged using data in which a related gene for predicting skin characteristics and a skin group classified according to skin characteristics are mapped.

11. The system of claim 1, wherein the cosmetic manufacturing system selects the cosmetic material to be discharged using data in which a skin group classified according to skin characteristics and cosmetic materials suitable for the skin group are mapped.

12. The system of claim 1, wherein the system further includes a key authentication server configured to share a public key with the terminal, encrypt a first server key using the public key to generate an encrypted first server key, and transmit the encrypted first server key to the terminal, wherein the terminal is configured to generate a second server key using the first server key and transmit the second server key to the key authentication server, wherein the key authentication server is further configured to decrypt the second server key using a master key and transmit the second server key to the gene/medical information server, and wherein the gene/medical information server is configured to transmit the genetic information or the medical information to the cosmetic manufacturing system upon receiving the second server key.

13. The system of claim 1, wherein the skin meter includes a light source and a sensor configured to acquire a normal light skin image and a fluorescent skin image from the user, wherein the system is configured to analyze a skin glycation grade by combining the normal light skin image and the fluorescent skin image to determine an amount of advanced glycation end products in a skin of the user, and wherein the cosmetic manufacturing system is further configured to select the cosmetic material by identifying a recommended ingredient capable of inhibiting the amount of the advanced glycation end products.

14. The system of claim 1, wherein the cosmetic manufacturing system includes:

a storage unit including a plurality of cartridges storing cosmetic materials;

a driving unit coupled to the plurality of cartridges; and a control unit configured to:

calculate a specific discharge ratio of the cosmetic materials based on the genetic information, and transmit a control signal to the driving unit to physically discharge and mix the at least one cosmetic material from the plurality of cartridges according to the specific discharge ratio to create a customized cosmetic formulation for the user.

* * * * *